(12) United States Patent
Horvath et al.

(10) Patent No.: US 8,758,290 B2
(45) Date of Patent: Jun. 24, 2014

(54) DEVICES AND METHODS FOR IMPLANTING A SHUNT IN THE SUPRACHOROIDAL SPACE

(75) Inventors: Christopher Horvath, Desert Hot Springs, CA (US); Ronald D. Bache, Mission Viejo, CA (US); Laszlo O. Romoda, San Clemente, CA (US); Guenther Grabner, Salzburg (AT); Herbert A. Reitsamer, Salzburg (AT); John R. Samples, Portland, OR (US)

(73) Assignee: AqueSys, Inc., Aliso Viejo, CA (US)

( * ) Notice: Subject to any disclaimer, the term of this patent is extended or adjusted under 35 U.S.C. 154(b) by 0 days.

(21) Appl. No.: 13/336,803

(22) Filed: Dec. 23, 2011

(65) Prior Publication Data

US 2012/0165722 A1 Jun. 28, 2012

Related U.S. Application Data

(63) Continuation-in-part of application No. 12/946,351, filed on Nov. 15, 2010, and a continuation-in-part of application No. 12/946,222, filed on Nov. 15, 2010.

(51) Int. Cl.
*A61M 5/00* (2006.01)
*A61F 11/00* (2006.01)

(52) U.S. Cl.
USPC .............................................. 604/8; 606/108

(58) Field of Classification Search
USPC ........ 604/8–10, 272, 523, 540–541; 606/107, 606/108, 166, 167; 128/898; 623/6.12, 623/1.11, 1.41, 4.1
See application file for complete search history.

(56) References Cited

U.S. PATENT DOCUMENTS

| 3,788,327 | A | 1/1974 | Donowitz et al. |
| 3,960,150 | A | 6/1976 | Hussain et al. |
| 4,722,724 | A | 2/1988 | Schocket |
| 4,750,901 | A | 6/1988 | Molteno |
| 4,787,885 | A | 11/1988 | Binder |
| 4,804,382 | A | 2/1989 | Turina et al. |
| 4,820,626 | A | 4/1989 | Williams et al. |
| 4,826,478 | A | 5/1989 | Schocket |
| 4,863,457 | A | 9/1989 | Lee |
| 4,902,292 | A | 2/1990 | Joseph |
| 4,911,161 | A | 3/1990 | Schechter |

(Continued)

FOREIGN PATENT DOCUMENTS

| WO | WO-98/23237 A1 | 6/1998 |
| WO | WO-02/74052 A2 | 9/2002 |
| WO | WO-2007/087061 A2 | 8/2007 |

*Primary Examiner* — Philip R Wiest
(74) *Attorney, Agent, or Firm* — James W. Hill; Mark Bentley; McDermott Will & Emery LLP

(57) ABSTRACT

The invention generally relates to devices and methods for implanting a shunt in the suprachoroidal space of an eye. In certain aspects, devices of the invention include a housing, a deployment mechanism at least partially disposed within the housing, and a flexible hollow shaft coupled to the deployment mechanism, in which the shaft holds an intraocular shunt, and is configured to self-guide the shunt along a scleral spur of an eye as the shunt is deployed from the shaft. Such a device may be inserted into an eye and used to deploy a shunt within the eye such that a proximal portion of the shunt receives fluid from an anterior chamber of an eye and a distal portion of the shunt directs the fluid to the suprachoroidal space.

19 Claims, 42 Drawing Sheets

(56) References Cited

U.S. PATENT DOCUMENTS

| | | | |
|---|---|---|---|
| 4,915,684 A | 4/1990 | MacKeen et al. | |
| 4,936,825 A | 6/1990 | Ungerleider | |
| 4,946,436 A | 8/1990 | Smith | |
| 4,968,296 A | 11/1990 | Ritch et al. | |
| 4,978,352 A | 12/1990 | Fedorov et al. | |
| 5,041,081 A | 8/1991 | Odrich | |
| 5,057,098 A | 10/1991 | Zelman | |
| 5,071,408 A | 12/1991 | Ahmed | |
| 5,092,837 A | 3/1992 | Ritch et al. | |
| 5,178,604 A | 1/1993 | Baerveldt et al. | |
| 5,180,362 A | 1/1993 | Worst | |
| 5,275,622 A | 1/1994 | Lazarus et al. | |
| 5,290,295 A | 3/1994 | Querals et al. | |
| 5,300,020 A | 4/1994 | L'Esperance, Jr. | |
| 5,338,291 A | 8/1994 | Speckman et al. | |
| 5,360,339 A | 11/1994 | Rosenberg | |
| 5,370,607 A | 12/1994 | Memmen | |
| 5,476,445 A | 12/1995 | Baerveldt et al. | |
| 5,516,522 A | 5/1996 | Peyman et al. | |
| 5,520,631 A | 5/1996 | Nordquist et al. | |
| 5,558,629 A | 9/1996 | Baerveldt et al. | |
| 5,558,630 A | 9/1996 | Fisher | |
| 5,601,094 A | 2/1997 | Reiss | |
| 5,665,093 A | 9/1997 | Atkins et al. | |
| 5,665,114 A | 9/1997 | Weadock et al. | |
| 5,670,161 A | 9/1997 | Healy et al. | |
| 5,695,474 A | 12/1997 | Daugherty | |
| 5,702,414 A | 12/1997 | Richter et al. | |
| 5,704,907 A | 1/1998 | Nordquist et al. | |
| 5,722,948 A | 3/1998 | Gross | |
| 5,743,868 A | 4/1998 | Brown et al. | |
| 5,763,491 A | 6/1998 | Brandt et al. | |
| 5,868,697 A | 2/1999 | Richter et al. | |
| 5,908,449 A | 6/1999 | Bruchman et al. | |
| 5,932,299 A | 8/1999 | Katoot | |
| 5,968,058 A | 10/1999 | Richter et al. | |
| 6,007,511 A * | 12/1999 | Prywes | 604/9 |
| 6,007,578 A | 12/1999 | Schachar | |
| 6,050,970 A | 4/2000 | Baerveldt | |
| 6,102,045 A | 8/2000 | Nordquist et al. | |
| 6,165,210 A | 12/2000 | Lau et al. | |
| 6,203,513 B1 | 3/2001 | Yaron et al. | |
| 6,228,873 B1 | 5/2001 | Brandt et al. | |
| 6,261,256 B1 | 7/2001 | Ahmed | |
| 6,264,665 B1 | 7/2001 | Yu et al. | |
| 6,280,468 B1 | 8/2001 | Schachar | |
| 6,450,937 B1 | 9/2002 | Mercereau et al. | |
| 6,450,984 B1 | 9/2002 | Lynch et al. | |
| 6,464,724 B1 | 10/2002 | Lynch et al. | |
| 6,468,283 B1 | 10/2002 | Richter et al. | |
| 6,510,600 B2 | 1/2003 | Yaron et al. | |
| 6,524,275 B1 | 2/2003 | Lynch et al. | |
| 6,533,768 B1 | 3/2003 | Hill | |
| 6,544,249 B1 | 4/2003 | Yu et al. | |
| 6,558,342 B1 | 5/2003 | Yaron et al. | |
| 6,595,945 B2 | 7/2003 | Brown | |
| 6,626,858 B2 | 9/2003 | Lynch et al. | |
| 6,638,239 B1 | 10/2003 | Bergheim et al. | |
| 6,666,841 B2 | 12/2003 | Gharib et al. | |
| 6,699,210 B2 | 3/2004 | Williams et al. | |
| 6,726,664 B2 | 4/2004 | Yaron et al. | |
| 6,736,791 B1 | 5/2004 | Tu et al. | |
| 6,780,164 B2 | 8/2004 | Bergheim et al. | |
| 6,783,544 B2 | 8/2004 | Lynch et al. | |
| 6,827,699 B2 | 12/2004 | Lynch et al. | |
| 6,827,700 B2 | 12/2004 | Lynch et al. | |
| 6,881,198 B2 | 4/2005 | Brown | |
| 6,939,298 B2 | 9/2005 | Brown et al. | |
| 6,955,656 B2 | 10/2005 | Bergheim et al. | |
| 6,981,958 B1 | 1/2006 | Gharib et al. | |
| 7,008,396 B1 | 3/2006 | Straub | |
| 7,037,335 B2 | 5/2006 | Freeman et al. | |
| 7,041,077 B2 | 5/2006 | Shields | |
| 7,118,547 B2 | 10/2006 | Dahan | |
| 7,135,009 B2 | 11/2006 | Tu et al. | |
| 7,163,543 B2 | 1/2007 | Smedley et al. | |
| 7,207,980 B2 | 4/2007 | Christian et al. | |
| 7,220,238 B2 | 5/2007 | Lynch et al. | |
| 7,331,984 B2 | 2/2008 | Tu et al. | |
| 7,431,710 B2 | 10/2008 | Tu et al. | |
| 7,458,953 B2 | 12/2008 | Peyman | |
| 7,563,241 B2 | 7/2009 | Tu et al. | |
| 7,625,384 B2 | 12/2009 | Eriksson et al. | |
| 7,867,186 B2 | 1/2011 | Haffner et al. | |
| 7,879,001 B2 | 2/2011 | Haffner et al. | |
| 8,277,437 B2 | 10/2012 | Saal et al. | |
| 8,308,701 B2 | 11/2012 | Horvath et al. | |
| 2002/0099434 A1 | 7/2002 | Buscemi et al. | |
| 2002/0133168 A1 | 9/2002 | Smedley et al. | |
| 2002/0177856 A1 | 11/2002 | Richter et al. | |
| 2002/0188308 A1 | 12/2002 | Tu et al. | |
| 2002/0193725 A1 | 12/2002 | Odrich | |
| 2003/0060752 A1 | 3/2003 | Bergheim et al. | |
| 2003/0079329 A1 | 5/2003 | Yaron et al. | |
| 2003/0093084 A1 | 5/2003 | Nissan et al. | |
| 2003/0229303 A1 | 12/2003 | Haffner et al. | |
| 2003/0236483 A1 | 12/2003 | Ren | |
| 2004/0024345 A1 | 2/2004 | Gharib et al. | |
| 2004/0050392 A1 | 3/2004 | Tu et al. | |
| 2004/0077987 A1 | 4/2004 | Rapacki et al. | |
| 2004/0088048 A1 | 5/2004 | Richter et al. | |
| 2004/0147870 A1 | 7/2004 | Burns et al. | |
| 2004/0225250 A1 | 11/2004 | Yablonski | |
| 2004/0254521 A1 | 12/2004 | Simon | |
| 2004/0260227 A1 | 12/2004 | Lisk, Jr. et al. | |
| 2005/0107734 A1 | 5/2005 | Coroneo | |
| 2005/0125003 A1 | 6/2005 | Pinchuk et al. | |
| 2005/0246023 A1 | 11/2005 | Yeung | |
| 2005/0266047 A1 | 12/2005 | Tu et al. | |
| 2005/0267398 A1 | 12/2005 | Protopsaltis et al. | |
| 2005/0277864 A1 | 12/2005 | Haffner et al. | |
| 2005/0288619 A1 | 12/2005 | Gharib et al. | |
| 2006/0106370 A1 | 5/2006 | Baerveldt et al. | |
| 2006/0116625 A1 | 6/2006 | Renati et al. | |
| 2006/0149194 A1 | 7/2006 | Conston et al. | |
| 2006/0173446 A1 | 8/2006 | Dacquay et al. | |
| 2007/0088242 A1 | 4/2007 | Coroneo | |
| 2007/0106235 A1 | 5/2007 | Coroneo | |
| 2007/0106236 A1 | 5/2007 | Coroneo | |
| 2007/0118065 A1 | 5/2007 | Pinchuk et al. | |
| 2007/0118066 A1 | 5/2007 | Pinchuk et al. | |
| 2007/0123812 A1 | 5/2007 | Pinchuk et al. | |
| 2007/0141116 A1 | 6/2007 | Pinchuk et al. | |
| 2007/0149915 A1 | 6/2007 | Yablonski | |
| 2007/0172903 A1 | 7/2007 | Toner et al. | |
| 2007/0191863 A1 | 8/2007 | De Juan et al. | |
| 2007/0233037 A1 | 10/2007 | Gifford, et al. | |
| 2008/0108933 A1 * | 5/2008 | Yu et al. | 604/8 |
| 2008/0195027 A1 | 8/2008 | Coroneo | |
| 2008/0228127 A1 * | 9/2008 | Burns et al. | 604/9 |
| 2008/0281277 A1 | 11/2008 | Thyzel | |
| 2008/0312661 A1 | 12/2008 | Downer et al. | |
| 2009/0036818 A1 | 2/2009 | Grahn et al. | |
| 2009/0043321 A1 | 2/2009 | Conston et al. | |
| 2009/0082863 A1 | 3/2009 | Schieber et al. | |
| 2009/0132040 A1 * | 5/2009 | Frion et al. | 623/6.12 |
| 2009/0182421 A1 | 7/2009 | Silvestrini et al. | |
| 2010/0010416 A1 | 1/2010 | Juan, Jr. et al. | |
| 2010/0087774 A1 | 4/2010 | Haffner et al. | |
| 2010/0090441 A1 | 4/2010 | Stettler | |
| 2010/0100104 A1 | 4/2010 | Yu et al. | |
| 2010/0114006 A1 | 5/2010 | Baerveldt | |
| 2010/0119696 A1 | 5/2010 | Yu et al. | |
| 2010/0121248 A1 | 5/2010 | Yu et al. | |
| 2010/0121249 A1 | 5/2010 | Yu et al. | |
| 2010/0134759 A1 | 6/2010 | Silvestrini et al. | |
| 2010/0137981 A1 | 6/2010 | Silvestrini et al. | |
| 2010/0152641 A1 | 6/2010 | Yablonski | |
| 2010/0234790 A1 | 9/2010 | Tu et al. | |
| 2010/0274258 A1 | 10/2010 | Silvestrini et al. | |
| 2010/0274259 A1 | 10/2010 | Yaron et al. | |
| 2010/0280317 A1 | 11/2010 | Silvestrini et al. | |
| 2011/0028884 A1 | 2/2011 | Theodore Coroneo | |
| 2011/0028983 A1 | 2/2011 | Silvestrini et al. | |

(56) References Cited

U.S. PATENT DOCUMENTS

| | | |
|---|---|---|
| 2011/0046536 A1 | 2/2011 | Stegmann et al. |
| 2011/0087148 A1 | 4/2011 | Silvestrini et al. |
| 2011/0087149 A1 | 4/2011 | Theodore Coroneo |
| 2011/0087150 A1 | 4/2011 | Theodore Coroneo |
| 2011/0087151 A1 | 4/2011 | Theodore Coroneo |
| 2011/0098627 A1 | 4/2011 | Wilcox |
| 2011/0105990 A1 | 5/2011 | Silvestrini |
| 2011/0112546 A1 | 5/2011 | Juan, Jr. et al. |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0238075 A1 | 9/2011 | Clauson et al. |
| 2012/0016286 A1 | 1/2012 | Silvestrini et al. |
| 2012/0022429 A1 | 1/2012 | Silvestrini et al. |
| 2012/0035524 A1 | 2/2012 | Silvestrini |
| 2012/0035525 A1 | 2/2012 | Silvestrini |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123430 A1 | 5/2012 | Horvath et al. |
| 2012/0123433 A1 | 5/2012 | Horvath et al. |
| 2012/0123434 A1 | 5/2012 | Grabner et al. |
| 2012/0123436 A1 | 5/2012 | Reitsamer et al. |
| 2012/0123437 A1 | 5/2012 | Horvath et al. |
| 2012/0123439 A1 | 5/2012 | Romoda et al. |
| 2012/0123440 A1 | 5/2012 | Horvath et al. |
| 2012/0165720 A1 | 6/2012 | Horvath et al. |
| 2012/0165721 A1 | 6/2012 | Grabner et al. |
| 2012/0165722 A1 | 6/2012 | Horvath et al. |
| 2012/0197175 A1 | 8/2012 | Horvath et al. |
| 2012/0220917 A1 | 8/2012 | Silvestrini et al. |
| 2013/0103145 A1 | 4/2013 | John et al. |
| 2013/0110125 A1 | 5/2013 | Silvestrini et al. |
| 2013/0149429 A1 | 6/2013 | Romoda et al. |
| 2013/0150770 A1 | 6/2013 | Horvath et al. |
| 2013/0253407 A1 | 9/2013 | Yablonski |
| 2013/0281817 A1 | 10/2013 | Schaller et al. |
| 2013/0281908 A1 | 10/2013 | Schaller et al. |

\* cited by examiner

DEVICES AND METHODS FOR IMPLANTING A SHUNT IN THE SUPRACHOROIDAL SPACE

RELATED APPLICATION

The present application is a continuation-in-part of U.S. nonprovisional patent application Ser. No. 12/946,351, filed Nov. 15, 2010, and is also a continuation-in-part of U.S. nonprovisional patent application Ser. No. 12/946,222, filed Nov. 15, 2010. The content of each of these applications is incorporated by reference herein its entirety.

FIELD OF THE INVENTION

The invention generally relates to devices and methods for implanting a shunt in the suprachoroidal space of an eye.

BACKGROUND

Glaucoma is a disease in which the optic nerve is damaged, leading to progressive, irreversible loss of vision. It is typically associated with increased pressure of the fluid (i.e., aqueous humor) in the eye. Untreated glaucoma leads to permanent damage of the optic nerve and resultant visual field loss, which can progress to blindness. Once lost, this damaged visual field cannot be recovered. Glaucoma is the second leading cause of blindness in the world, affecting 1 in 200 people under the age of fifty, and 1 in 10 over the age of eighty for a total of approximately 70 million people worldwide.

The importance of lowering intraocular pressure (IOP) in delaying glaucomatous progression has been well documented. When drug therapy fails, or is not tolerated, surgical intervention is warranted. Surgical filtration methods for lowering intraocular pressure by creating a fluid flow-path between the anterior chamber and the subconjunctival tissue have been described. One particular ab interno glaucoma filtration method has been described whereby an intraocular shunt is implanted by directing a needle which holds the shunt through the cornea, across the anterior chamber, and through the trabecular meshwork and sclera, and into the subconjunctival space. See, for example, U.S. Pat. No. 6,544,249, U.S. patent application publication number 2008/0108933, and U.S. Pat. No. 6,007,511. Avoiding damage to the conjunctiva (e.g., subconjunctival blebbing which leads to conjunctival leakage, infections, and endophthalmitis) is critical in determining the success or failure of subconjunctival glaucoma filtration surgery.

To avoid the risk of damaging the conjunctiva, methods have been developed for implanting shunts in the suprachoroidal space. Such methods generally involve implanting rigid shunts that need to be anchored to tissue adjacent to the suprachoroidal space. Implanting a rigid shunt into the suprachoroidal space may result in the shunt producing a cyclodialysis cleft, or separation of the ciliary body from the scleral spur, creating hypotony by allowing the uncontrolled escape of aqueous humor through the cleft into the suprachoroidal space. Similarly, anchoring of the shunt to the tissue adjacent the suprachoroidal space may also result in formation of a cyclodialysis cleft.

SUMMARY

The present invention provides devices and methods for self-guided implantation of soft gel tissue compliant intraocular shunts in the suprachoroidal space. Shunt placement in the suprachoroidal space avoids contact with the conjunctiva, thus safeguarding the integrity of the conjunctiva. Implanting shunts made of soft, tissue compliant material avoid the creation of a cyclodialysis cleft and reduces or eliminates the risk of hypotony and related side effects.

Devices of the invention accomplish self-guided shunt deployment in the suprachoroidal space by having a flexible hollow shaft with a bend that biases the shunt to follow the scleral spur as it is deployed from the shaft. The hollow shaft is pre-bent to match the angle or arc of the sclera. In a pre-deployment configuration, the shaft is disposed within the device. The rigidity of the device holds the hollow shaft in a straight configuration. Upon its exposure from the device, the hollow shaft reverts to its pre-bent configuration. Such a pre-bend allows the hollow shaft to follow the scleral spur down along the sclera in a self-guided manner to the suprachoroidal space. Additionally, the flexibility of the hollow shaft allows it to continually bend and flex in response to the anatomy as the hollow shaft advances from the device. Once properly positioned, the shunt is deployed from the shaft. The bend in the shaft self-guides the shunt along the scleral spur of the eye as the shaft is retracted into the device and the shunt is deployed from the shaft.

In certain aspects, devices of the invention also include a housing and a deployment mechanism at least partially disposed in the housing. In certain embodiments, the hollow shaft is coupled to the deployment mechanism. The housing may include two components, a proximal portion and a distal portion. The components are configured such that the distal portion is movable within the proximal portion. In certain embodiments, the distal portion of the housing includes a stiff sleeve and the shaft is movably disposed within the sleeve. In other embodiments, the distal portion is without a stiff outer sleeve. As previously described, the shaft is flexible and pre-bent to match an angle of the sclera. In certain embodiments, the distal end of the hollow shaft includes a sharp tip to assist in piercing the sclera. In certain embodiments, the hollow shaft is a flexible needle.

In other embodiments, a distal end of the sleeve further includes a protrusion. The protrusion may be formed integrally with the distal end of the sleeve or may be connected to a distal end of the sleeve. The protrusion may surround the distal end of the sleeve, or the protrusion may extend around only a portion of the sleeve. In certain embodiments, the protrusion is a collar that surrounds the distal end of the sleeve. In other embodiments, the protrusion includes a flat bottom portion and an angled top portion. In particular embodiments, the angle of the top portion is substantially identical to an anterior chamber angle of an eye.

Devices of the invention include numerous configurations, such as an insertion configuration, a shaft exposure configuration, and a deployment configuration. The insertion configuration includes the hollow shaft fully disposed within the sleeve. The shaft exposure configuration includes retraction of the distal portion of the housing to at least partially within the proximal portion of the housing, thereby exposing a distal portion of the hollow shaft from the sleeve.

The deployment configuration involves engagement of the deployment mechanism. In certain embodiments, the deployment mechanism may include a two stage system. The first stage is a pusher component and the second stage is a retraction component. Rotation of the deployment mechanism sequentially engages the pusher component and then the retraction component. The pusher component pushes the shunt to partially deploy the shunt from within the shaft, and the retraction component retracts the shaft from around the shunt. The deployment mechanism further includes at least one member that limits axial movement of the shaft.

Devices of the invention may be completely automated, partially automated, or completely manual. Devices of the invention may be connected to larger robotic systems or may be used as stand alone handheld deployment devices. In particular embodiments, the device is a handheld device.

Devices of the invention may include an indicator that provides feedback to an operator as to the state of the deployment mechanism. The indicator may be any type of indicator know in the art, for example a visual indicator, an audio indicator, or a tactile indicator. In certain embodiments, the indicator is a visual indicator.

Other aspects of the invention provide for methods of using the above described devices for inserting a intraocular shunt into the suprachoroidal space of an eye. Such methods involve inserting the above device into an eye and deploying a shunt from the device within the eye such that a proximal portion of the shunt receives fluid from an anterior chamber of an eye and a distal portion of the shunt directs the fluid to the suprachoroidal space. Methods of the invention may also involve injecting a drug into the suprachoroidal space prior to deploying the shunt from the device. Exemplary drugs include drug is a BSS/steroids or antifibrotic agents.

Methods of the invention are typically conducted using an ab interno approach. Such an approach is contrasted with an ab externo approach, which involves inserting the shaft through the conjunctiva of the eye. Although, methods of the invention may be conducted using an ab externo approach.

Methods of the invention may be performed such that the shaft is inserted above or below the corneal limbus. Methods of the invention may be performed such that the shaft is inserted into the eye without removing an anatomical feature of the eye, such as the trabecular meshwork, the iris, the cornea, and the aqueous humor. In certain embodiments, methods of the invention may be conducted without substantial subconjunctival blebbing.

BRIEF DESCRIPTION OF THE DRAWINGS

FIG. 2B is a side view of the protrusion shown in FIG. 2A. FIG. 2C is a top view of the protrusion shown in FIG. 2A.

FIG. 4 shows the shaft in a straight configuration, as if it is within the stiff outer sleeve.

FIGS. 5A-D show the shaft in a straight configuration, as if it is within the stiff outer sleeve.

FIG. 6C shows the shaft in a straight configuration, as if it is within the stiff outer sleeve.

FIG. 8 shows the shaft in a straight configuration, as if it is within the stiff outer sleeve.

FIG. 10A is a magnified view of the position of the distal portion of the device relative to the proximal portion of the device in the insertion configuration. FIG. 10B is a magnified view of the sleeve of the device inserted into the eye. This figure also shows the sleeve and protrusion fitted within an anterior chamber angle of the eye.

FIG. 11A is a magnified view of the position of the distal portion of the device relative to the proximal portion of the device. FIG. 11B is a magnified view of the sleeve of the device inserted into the eye.

FIGS. 12A-B show the shaft in a straight configuration, as if it is within the stiff outer sleeve.

FIG. 13A is a magnified view of the position of the distal portion of the device relative to the proximal portion of the device. FIG. 13B is a magnified view of the sleeve of the device inserted into the eye and the shaft extended from the sleeve.

FIG. 14B is a magnified view of the position of the distal portion of the device relative to the proximal portion of the device. FIG. 14C is a magnified view of the sleeve of the device inserted into the eye, retraction of the shaft into the sleeve, and the shunt being deployed from the sleeve.

FIG. 15A is a magnified view of the position of the distal portion of the device relative to the proximal portion of the device. FIG. 15B is a magnified view of the sleeve of the device being removed from the eye FIG. 16 provides a schematic of a shunt having a flexible portion.

FIG. 8A shows an embodiment of a shunt in which the proximal portion of the shunt includes more than one port and the distal portion of the shunt includes a single port. FIG. 8B shows another embodiment of a shunt in which the proximal portion includes a single port and the distal portion includes more than one port. FIG. 8C shows another embodiment of a shunt in which the proximal portions include more than one port and the distal portions include more than one port.

DETAILED DESCRIPTION

The invention generally relates to devices and methods of using such devices for implanting a shunt in the suprachoroidal space. In certain aspects, devices of the invention include a housing, a deployment mechanism at least partially disposed within the housing, and a flexible hollow shaft coupled to the deployment mechanism, in which the shaft holds an intraocular shunt, and is configured to self-guide the shunt along a scleral spur of an eye as the shunt is deployed from the device. Such devices may be inserted into an eye and used to deploy a shunt within the eye such that a proximal portion of the shunt receives fluid from an anterior chamber of an eye and a distal portion of the shunt directs the fluid to the suprachoroidal space.

Devices and Methods for Shunt Placement in the Suprachoroidal Space

Figure 1A:
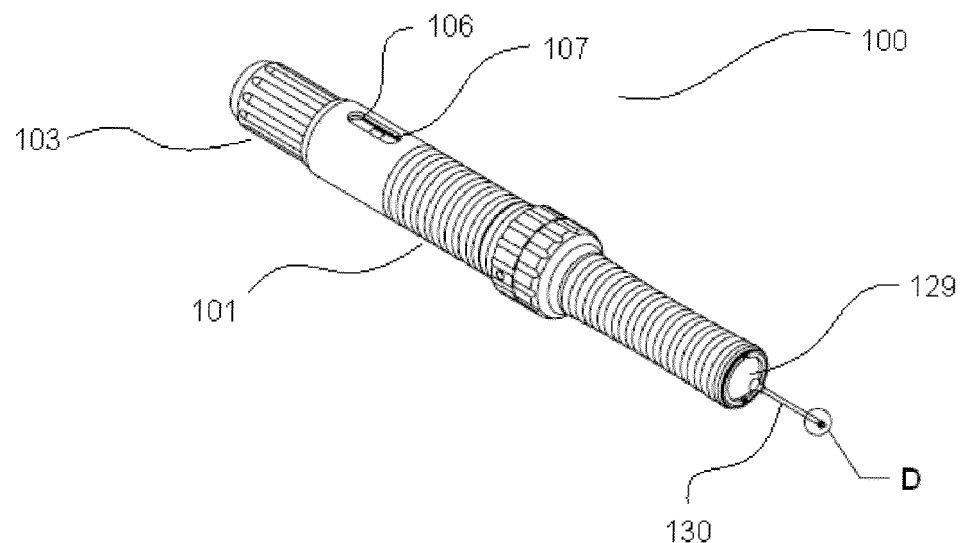
FIG. 1A is a schematic showing an embodiment of a shunt deployment device according to the invention.

Reference is now made to FIG. 1A which shows an embodiment of a shunt deployment device 100 according to the invention. While FIG. 1 shows a handheld manually operated shunt deployment device, it will be appreciated that devices of the invention may be coupled with robotic systems and may be completely or partially automated. As shown in FIG. 1A deployment device 100 includes a generally cylindrical body or housing 101, however, the body shape of housing 101 could be other than cylindrical. Housing 101 may have an ergonomic shape, allowing for comfortable grasping by an operator. Housing 101 is shown with optional grooves 102 to allow for easier gripping by a surgeon.

Figure 1D:
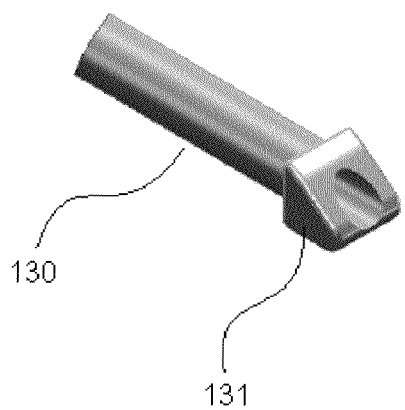
FIG. 1D is a schematic showing an enlarged view of a protrusion on a distal end of a distal portion of a housing of the device of FIG. 1A. In this figure, a bottom portion of the protrusion is flat and a top portion of the protrusion is angled.
Figure 1B:
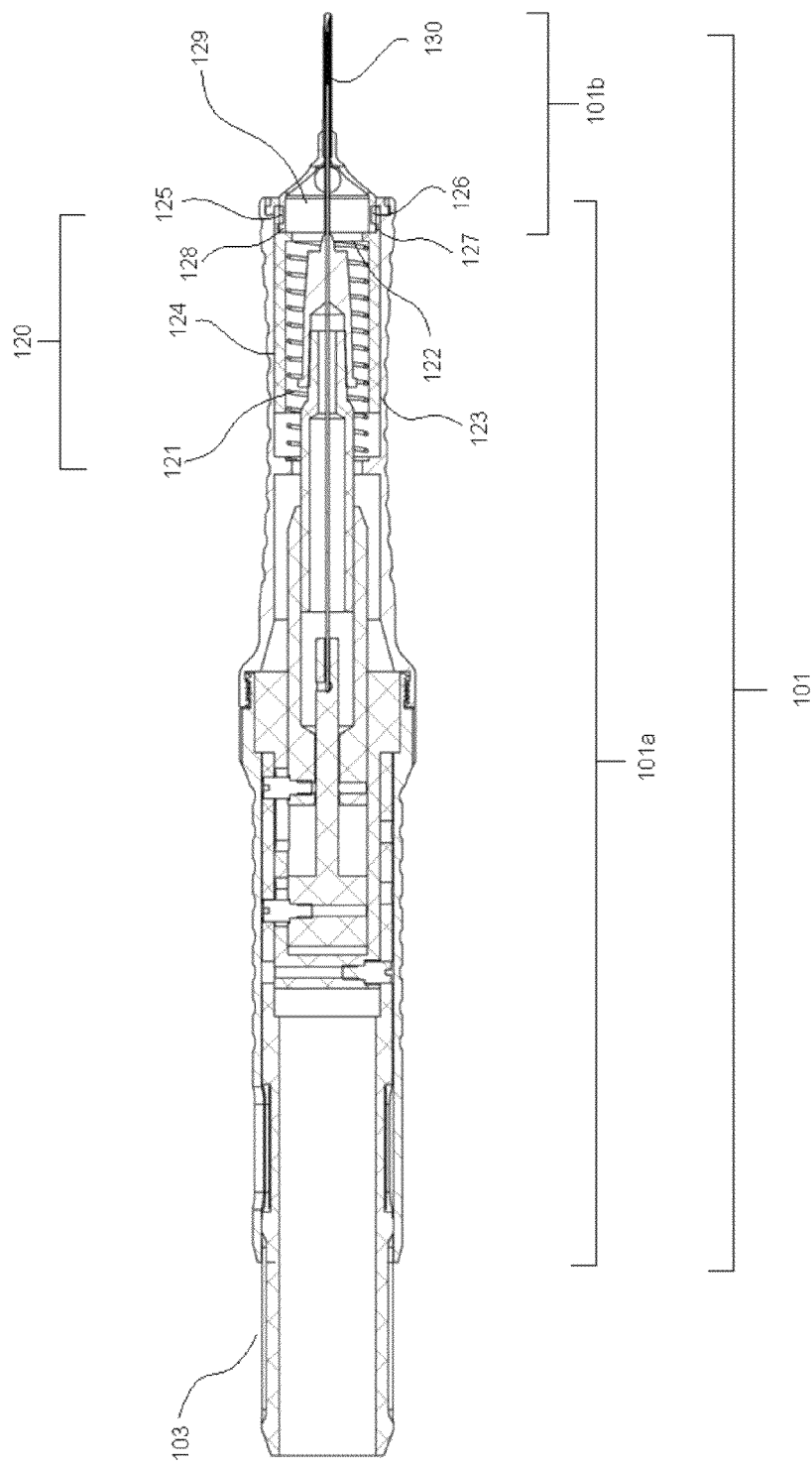
FIG. 1B shows a cross sectional view of the device of FIG. 1. In this figure, the distal portion of the housing is extended from the proximal portion of the housing.

FIG. 1B shows a cross sectional view of device 100. This figure shows that housing 101 includes a proximal portion 101a and a distal portion 101b. The distal portion 101b is movable within proximal portion 101a. In this figure, spring mechanism 120 includes a spring 121 that controls movement of distal portion 101b. Spring mechanism 120 further includes a member 122 that acts as a stopper and limits axial retraction of distal portion 101b within proximal portion 101a. Spring mechanism 120 further includes members 123 and 124 that run the length of spring 121. The ends of members 123 and 124 include flanges 125 and 126 that project inward from members 123 and 124. An end of distal portion 101b includes flanges 127 and 128 that project outward from distal portion 101b. Flanges 125 and 126 interact with flanges 127 and 128 to prevent release of distal portion 101b from proximal portion 101a. The flanges 125 and 126 and 127 and 128 hold the distal portion 101b in an extended position until a compressive force acts upon distal portion 101b, thereby causing distal portion 101b to partially retract within proximal portion 101a.

Figure 1C:
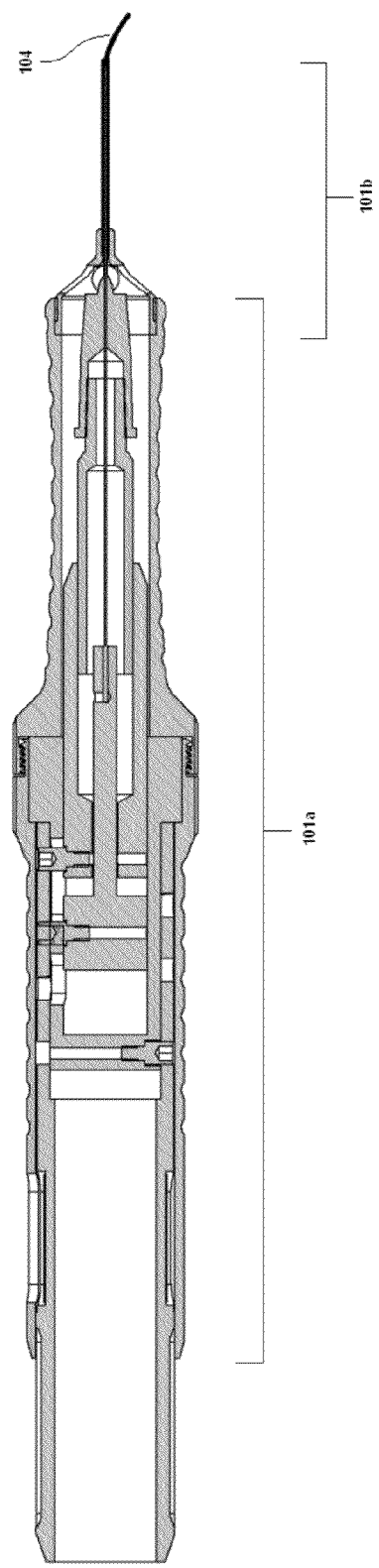
FIG. 1C shows a cross sectional view of the device of FIG. 1. In this figure, the distal portion of the housing is retracted within the proximal portion of the housing.

Distal portion 101b includes a capsule 129 and an outer stiff hollow sleeve 130. Capsule 129 and sleeve 130 may be formed integrally or may be separate components that are coupled or connected to each other. The hollow sleeve 130 is configured for insertion into an eye and to extend into an anterior chamber of an eye. FIG. 1B shows distal portion 101b of housing 101 extended from proximal portion 101a of housing 101. In this configuration, an inner hollow shaft 104 (not shown in this figure) is completely disposed within sleeve 130. FIG. 1C shows distal portion 101b of housing 101 retracted within proximal portion 101a of housing 101. Retraction of distal portion 101b of housing 101 within proximal portion 101a of housing 101 exposes hollow shaft 104. The hollow shaft 104 may include a sharpened distal end. The hollow shaft 104 is flexible and pre-bent to follow the scleral spur down along the sclera upon extension of the hollow shaft 104 from the sleeve 130, which is discussed in greater detail below. The material used for the hollow shaft 104 may be any memory shape material, such as spring steel, such that the hollow shaft 104 can easily transform from its bent position to a straight cannula when housed within the sleeve 130.

A distal end of sleeve 130 may optionally include a protrusion 131 (FIG. 1D). Protrusion 131 provides resistance feedback to an operator as the operator is advancing the sleeve 130 through an anterior chamber of an eye. In a standard ab interno approach (see for example Yu et al. U.S. Pat. No. 6,544,249 and U.S. patent application number 2008/0108933) a deployment device holding a shunt enters an eye through a cornea. The deployment device is advanced across the anterior chamber in what is referred to as a transpupil implant insertion. The deployment device is advanced to the sclera on the opposite side of the eye from which the device entered the eye. In embodiments that have the protrusion 131 at the distal end of sleeve 130, upon advancement of the device 100 across an anterior chamber of the eye, the protrusion 131 at the distal end of the hollow sleeve 130 will contact the sclera, providing resistance feedback to an operator that no further advancement of the device 100 is necessary. This feedback also informs the operator that the device 100 is in proper position for exposure of the hollow shaft 104, which will advance through the sclera for deployment of an intraocular shunt. The protrusion 131, provides adequate surface area at the distal end of sleeve 130, thus preventing sleeve 130 from entering the sclera.

Figure 2A:
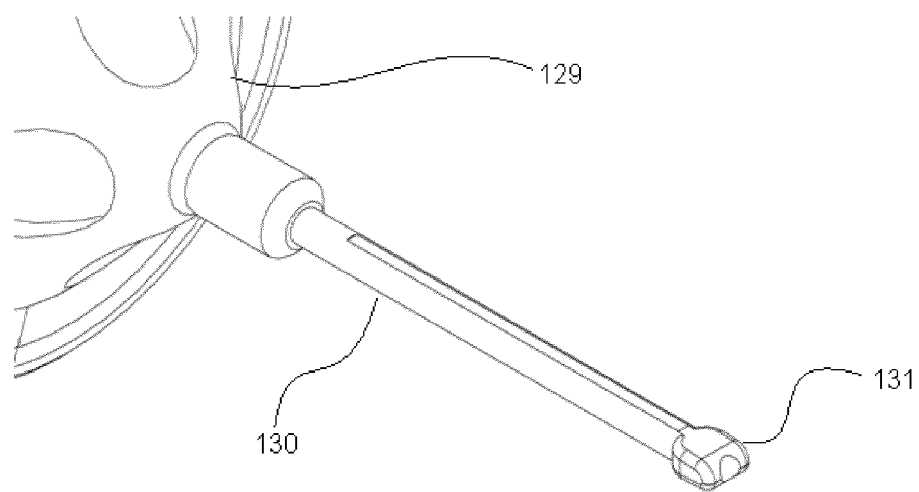
FIGS. 2A-2C are schematics showing an enlarged view of a protrusion on a distal end of a distal portion of a housing of devices of the invention.
Figure 2B:
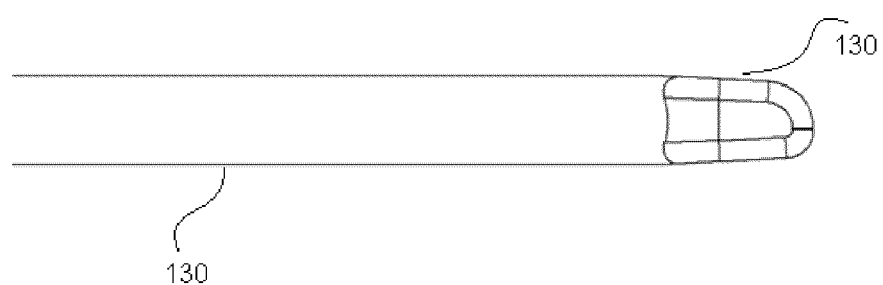
Figure 2C:
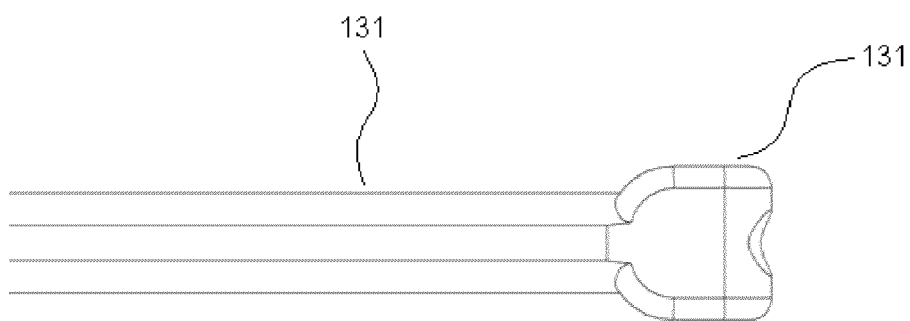

In certain embodiments, protrusion 131 has a substantially flat bottom portion and an angled top portion (FIG. 1D). In other embodiments, protrusion 131 has a slightly tapered top and a slightly tapered bottom with a rounded distal portion (FIGS. 2A-2C).

Figure 3A:
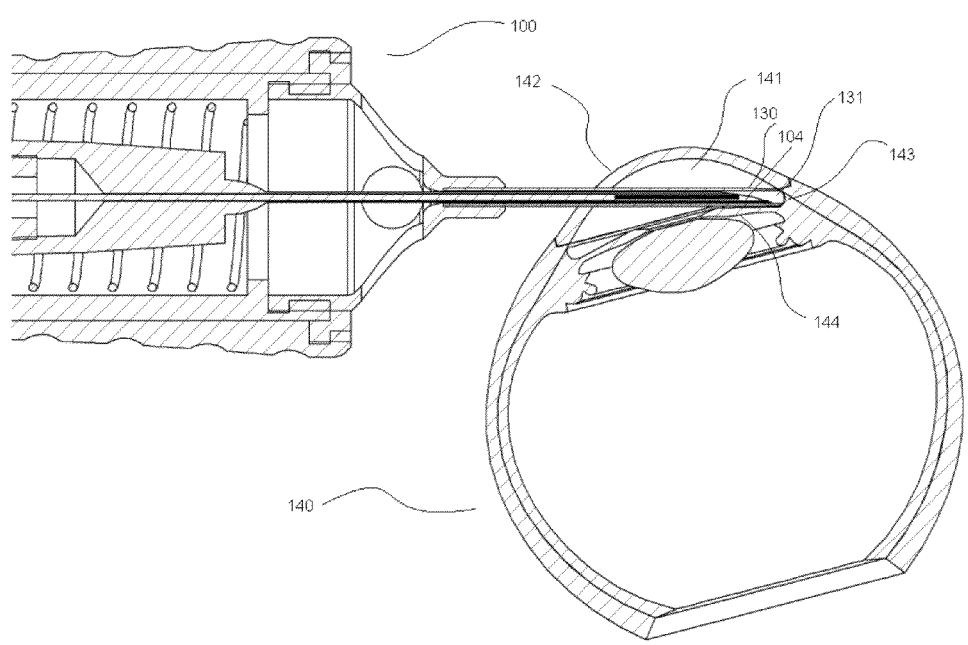
FIG. 3A shows a deployment device in an insertion configuration and fit into an anterior chamber of an eye.
Figure 3B:
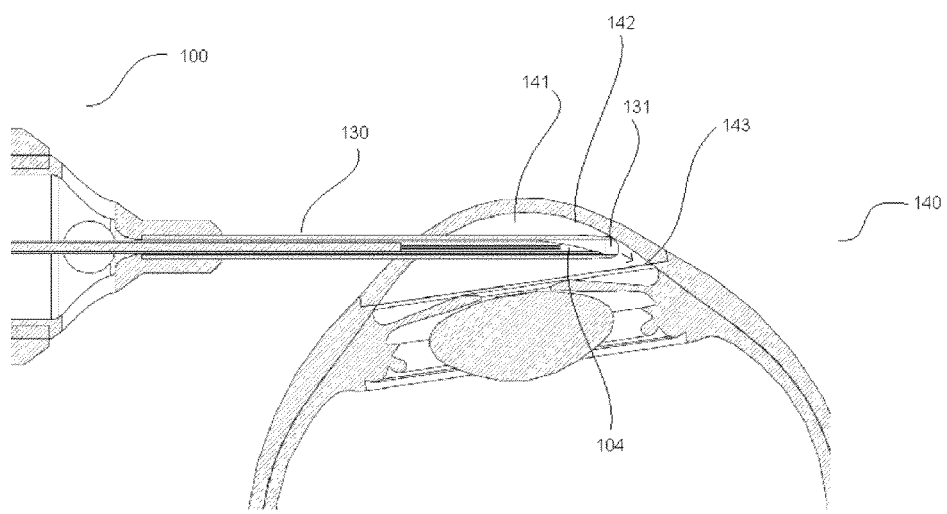
FIG. 3B shows a deployment device in an insertion configuration and inserted at too shallow an angled, thus abutting the sclera above the anterior chamber angle.
Figure 3C:
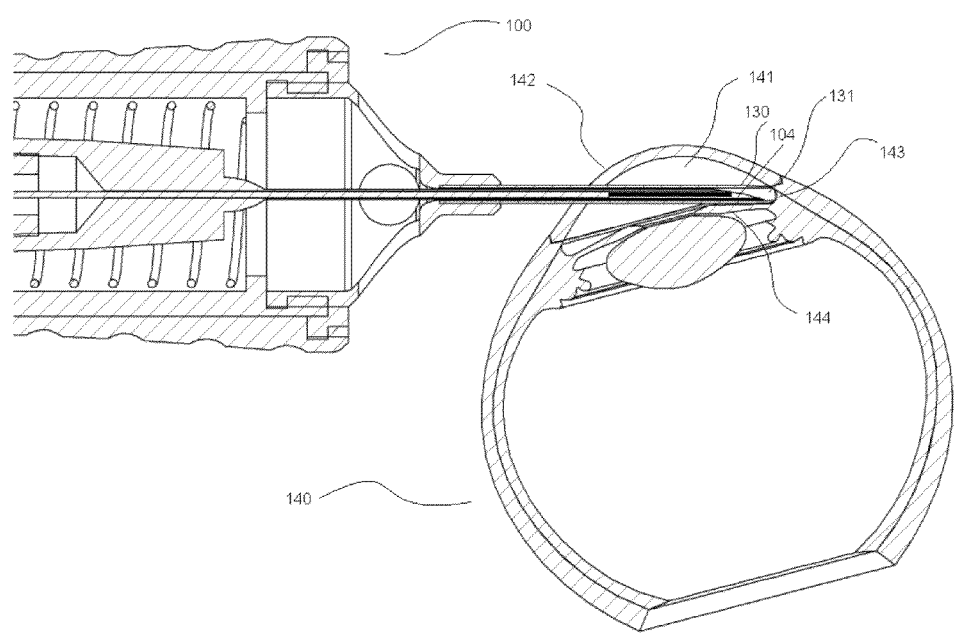
FIG. 3C shows a deployment device in an insertion configuration after the protrusion has caused the device to slide down the sclera and be fit into an anterior chamber of an eye.

Referring back to FIG. 1D, the angle of the top portion is substantially identical to an anterior chamber angle of an eye. Such a shape of the protrusion ensures that the device of the invention will also find its way to fit into the anterior chamber angle of the eye, the place for proper deployment of an intraocular shunt. This is explained with reference to FIGS. 3A to 3E. FIG. 3A shows device 100 in an insertion configuration and inserted into an eye 140. In this figure, protrusion 131 at the distal end of the sleeve 130 has been advanced across the anterior chamber 141 to the sclera 142 on the opposite side of the eye 140 from which the device entered the eye 140. FIG. 3A shows protrusion 131 fitted within the anterior chamber angle 143 of the eye 140. If sleeve 130 enters the anterior chamber 141 at too shallow an angle, i.e., the protrusion 131 hit the sclera 142 above the anterior chamber angle 143, the angled top portion of the protrusion 131 causes the sleeve 130 to slide down the sclera 142 (direction of arrow) until the protrusion 131 is fit within the anterior chamber angle 143 of the eye 140 (FIGS. 3B and 3C). The sleeve 130 will slide down the sclera 142 instead of entering the sclera 142 at the contact point because the hollow shaft 104 is completely disposed within the sleeve 130 and the protrusion 131 provides adequate surface area at the distal end of sleeve 130 to prevent enough force from being generated at the distal end of sleeve 130 that would result in sleeve 130 entering the sclera 142.

Figure 3D:
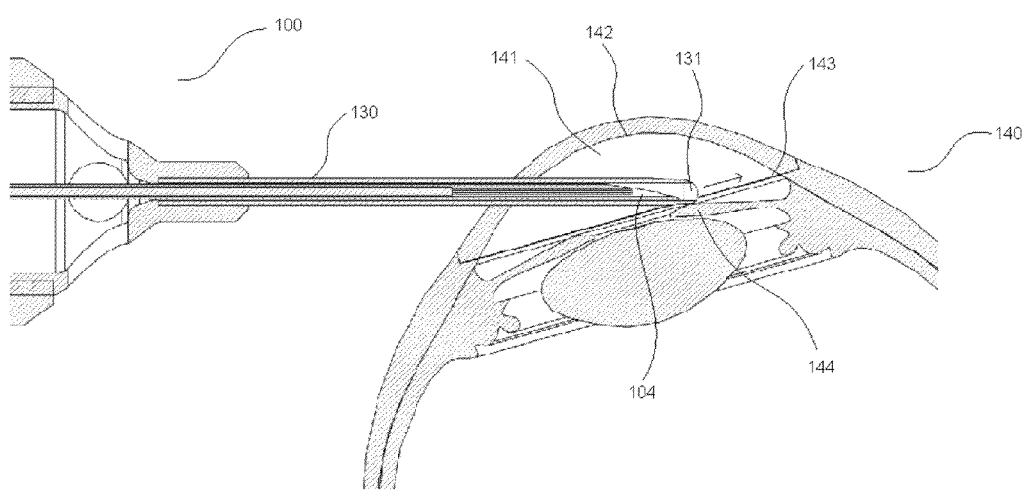
FIG. 3D shows a deployment device in an insertion configuration and inserted at too steep an angled, thus abutting the iris below the anterior chamber angle.
Figure 3E:
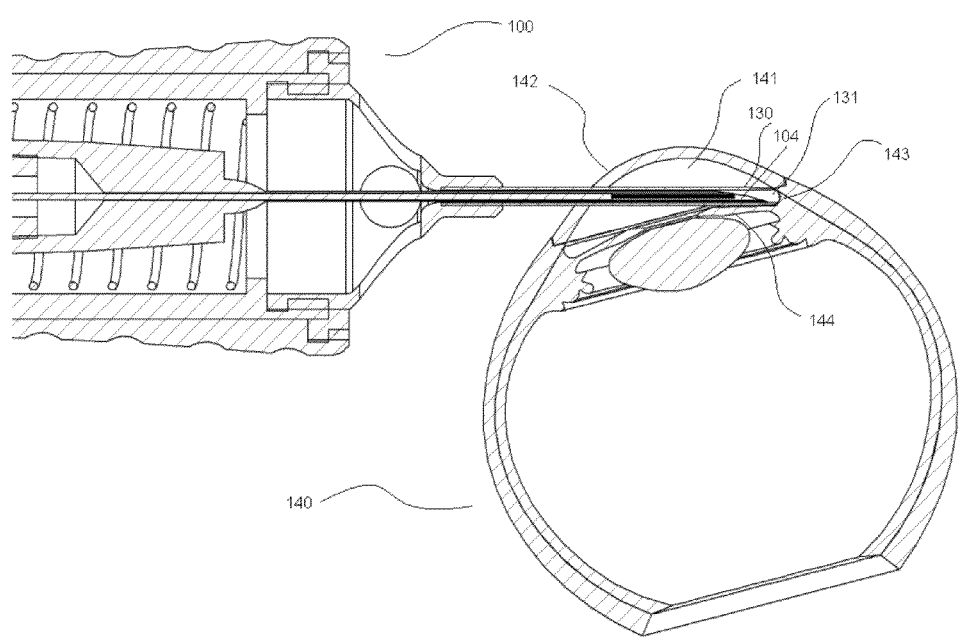
FIG. 3E shows a deployment device in an insertion configuration after the protrusion has caused the device to deflect off of the iris and slide along the iris and be fit into an anterior chamber of an eye.

Conversely, if sleeve 130 enters the anterior chamber 141 at too steep an angle, i.e., the protrusion 131 hit the iris 144 below the anterior chamber angle 143, the substantially flat bottom portion of the protrusion 131 causes the sleeve 130 to deflect off the iris 144 and proceed in a direction parallel to the iris 144 until the protrusion 131 is fit within the anterior chamber angle 143 of the eye 140 (FIGS. 3D and 3E). The sleeve 130 will deflect off the iris 144 instead of entering the iris 144 at the contact point because the hollow shaft 104 is completely disposed within the sleeve 130 and the protrusion 131 provides adequate surface area at the distal end of sleeve 130 to prevent enough force from being generated at the distal end of sleeve 130 that would result in sleeve 130 entering the iris 144.

In certain embodiments, protrusion 131 is not required. In these embodiments, the sleeve 130 is of a sufficient outer diameter such that the sleeve itself may serve the function of the protrusion as described above. In these embodiments, a distal end of the sleeve is shaped to have a flat bottom portion and an angled top portion. In other embodiments, a goniolens is used to visualize advancement of the device within the eye, and thus the configuration of the distal end of the sleeve 130 is not important for proper shunt deployment using devices of the invention.

Referring back to FIG. 1A, the proximal portion 101a of the housing 101 is open at its proximal end, such that a portion of a deployment mechanism 103 may extend from the proximal end of the proximal portion 101a of the housing 101. The sleeve 130 of the distal portion 101b of the housing 101 is also open such that at least a portion of the hollow shaft 104 may extend inside the housing, into sleeve 130 of the distal portion 101b of the housing 101, and extend beyond the distal end of the sleeve 130 in certain configurations (such as the deployment configuration). Housing 101 further includes a slot 106 through which an operator, such as a surgeon, using the device 100 may view an indicator 107 on the deployment mechanism 103.

Housing 101 and protrusion 131 may be made of any material that is suitable for use in medical devices. For example, housing 101 and protrusion 131 may be made of a lightweight aluminum or a biocompatible plastic material. Examples of such suitable plastic materials include polycarbonate and other polymeric resins such as DELRIN and ULTEM. In certain embodiments, housing 101 and protrusion 131 are made of a material that may be autoclaved, and thus allow for housing 101 and protrusion 131 to be re-usable. Alternatively, device 100, may be sold as a one-time-use device, and thus the material of the housing and the protrusion does not need to be a material that is autoclavable.

Figure 4:
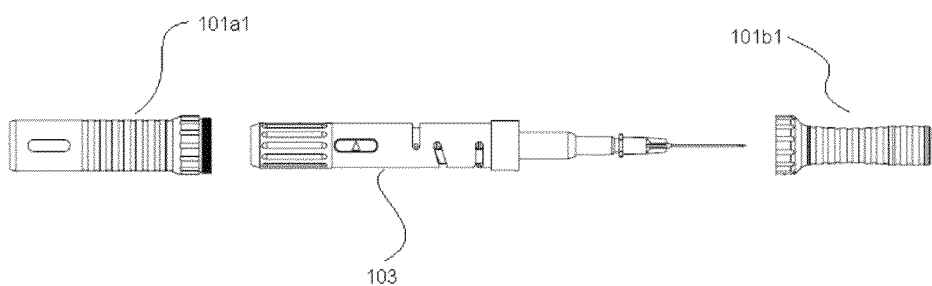
FIG. 4 shows an exploded view of the device shown in FIG. 1.
Figure 5A:
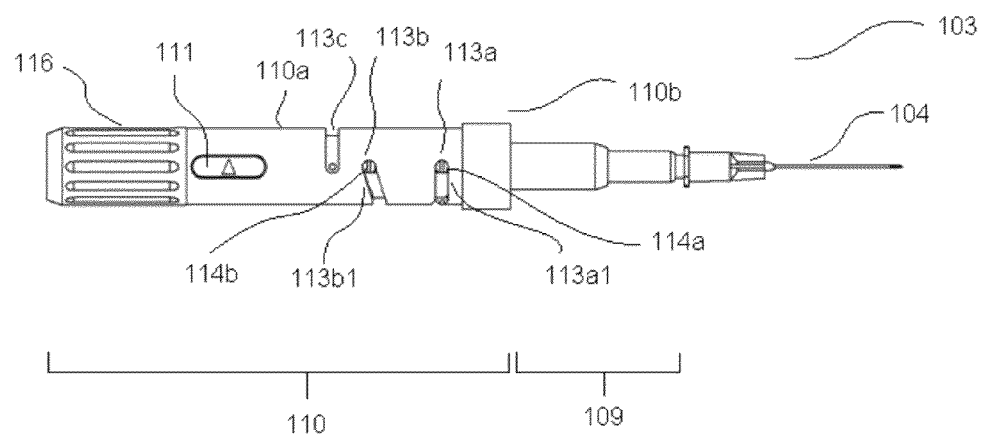
FIGS. 5A-D are schematics showing different enlarged views of the deployment mechanism of the deployment device.
Figure 5B:
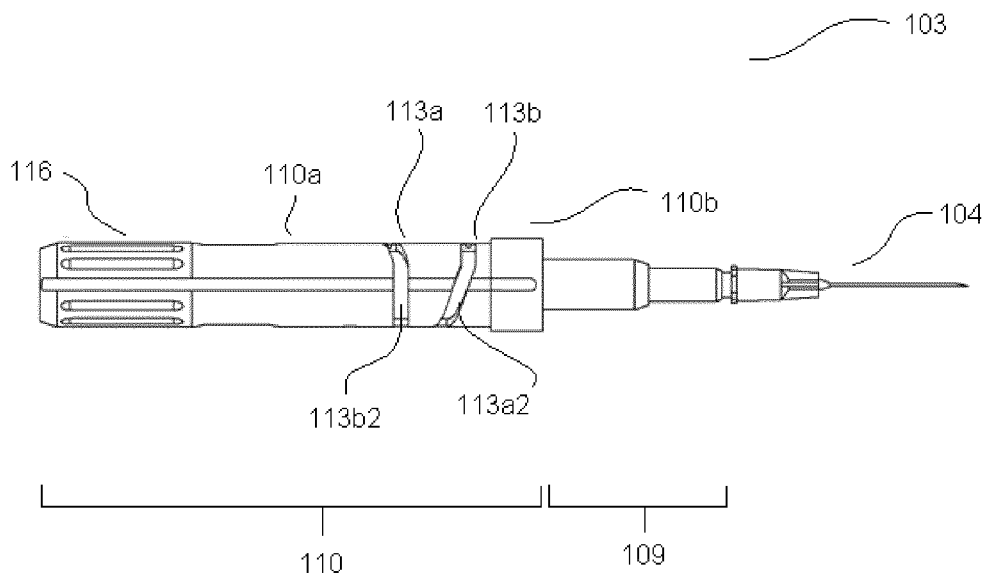
Figure 5C:
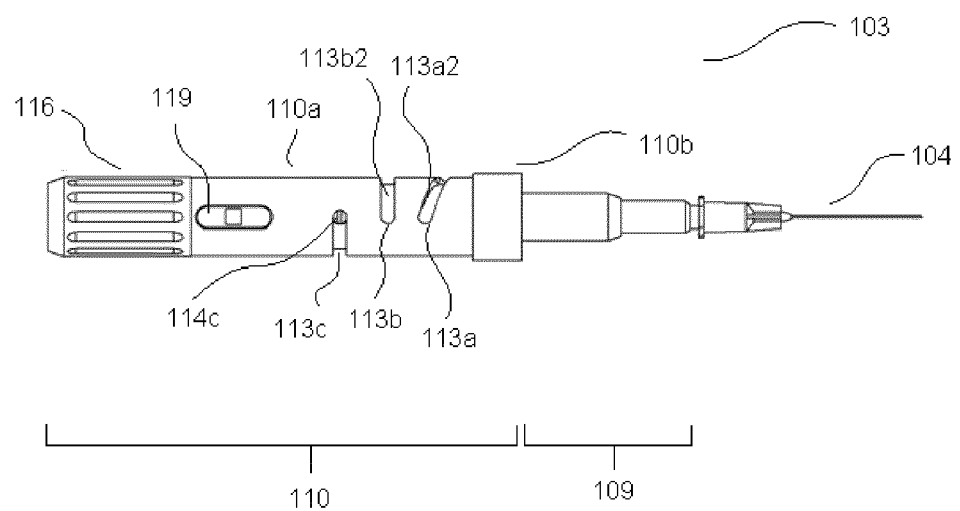
Figure 5D:
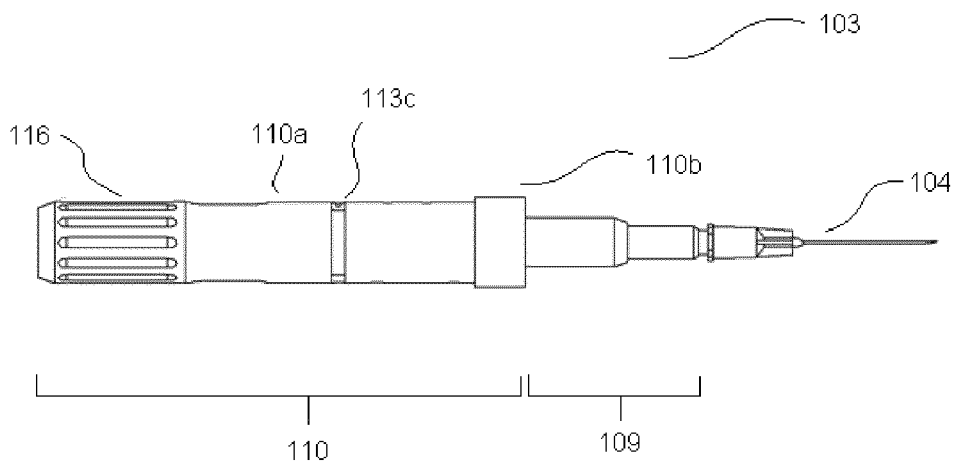

The proximal portion 101a of housing 101 may be made of multiple components that connect together to form the housing. FIG. 4 shows an exploded view of deployment device 100. FIG. 4 shows the shaft in a straight configuration, as if it is within the stiff outer sleeve. In this figure, proximal portion 101a of housing 101, is shown having two components 101a1 and 101a2. The components are designed to screw together to form proximal portion 101a of housing 101. FIG. 5 also shows deployment mechanism 103. The housing 101 is designed such that deployment mechanism 103 fits within assembled housing 101. Housing 101 is designed such that components of deployment mechanism 103 are movable within housing 101. Hollow shaft 104 is shown in these figures in its straightened configuration, as if it were housed within the outer sleeve 130.

FIGS. 5A-D show different enlarged views of the deployment mechanism 103. FIGS. 5A-D show the shaft in a straight configuration, as if it is within the stiff outer sleeve. Deployment mechanism 103 may be made of any material that is suitable for use in medical devices. For example, deployment mechanism 103 may be made of a lightweight aluminum or a biocompatible plastic material. Examples of such suitable plastic materials include polycarbonate and other polymeric resins such as DELRIN and ULTEM. In certain embodiments, deployment mechanism 103 is made of a material that may be autoclaved, and thus allow for deployment mechanism 103 to be re-usable. Alternatively, device 100 may be sold as a one-time-use device, and thus the material of the deployment mechanism does not need to be a material that is autoclavable.

Deployment mechanism 103 includes a proximal portion 109 and a distal portion 110. The deployment mechanism 103 is configured such that proximal portion 109 is movable within distal portion 110. More particularly, proximal portion 109 is capable of partially retracting to within distal portion 110.

In this embodiment, the proximal portion 109 is shown to taper to a connection with a hollow shaft 104. This embodiment is illustrated such that the connection between the hollow shaft 104 and the proximal portion 109 of the deployment mechanism 103 occurs inside the housing 101. Hollow shaft 104 may be removable from the proximal portion 109 of the deployment mechanism 103. Alternatively, the hollow shaft 104 may be permanently coupled to the proximal portion 109 of the deployment mechanism 103.

Figure 7:
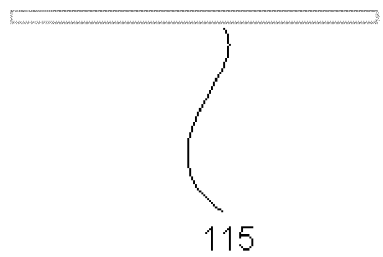
FIG. 7 depicts a schematic of an exemplary intraocular shunt.

Generally, hollow shaft 104 is configured to hold an intraocular shunt 115. An exemplary intraocular shunt 115 in shown in FIG. 7. Other exemplary intraocular shunts are described in greater detail below. Generally, in one embodiment, intraocular shunts are of a cylindrical shape and have an outside cylindrical wall and a hollow interior. The shunt may have an inner diameter of approximately 50 µm to approximately 250 µm, an outside diameter of approximately 80 µm to approximately 300 µm, and a length of approximately 0.5 mm to about 20 mm. Thus, hollow shaft 104 is configured to at least hold a shunt of such shape and such dimensions. In particular embodiments, the hollow shaft has an inner diameter of approximately 200 µm to approximately 400 µm. However, hollow shaft 104 may be configured to hold shunts of different shapes and different dimensions than those described above, and the invention encompasses an hollow shaft 104 that may be configured to hold any shaped or dimensioned intraocular shunt. In certain embodiments, the shunt is a soft gel shunt, e.g., a gelatin shunt. If a gelatin shunt is used, the shunt is generally wetted inside the hollow shaft 104 with a balanced salt solution (e.g., Dulbecco's Phosphate Buffered Saline) or a steroid or other drug prior to implantation. Such priming ensures that the shunt remains flexible before implantation.

The hollow shaft 104 may be any length. A usable length of the hollow shaft may be anywhere from about 5 mm to about 40 mm, and is 15 mm in certain embodiments. In other embodiments, a distal end of the hollow shaft is beveled or is sharpened to a point. In particular embodiments, the shunt is held completely within the hollow interior of the hollow shaft 104. In certain embodiments, the hollow shaft is a needle having a hollow interior. Needles that are configured to hold an intraocular shunt are commercially available from Terumo Medical Corp. (Elkington, Md.).

A distal portion of the deployment mechanism 103 includes optional grooves 116 to allow for easier gripping by an operator for easier rotation of the deployment mechanism, which will be discussed in more detail below. The distal portion 110 of the deployment mechanism also includes at least one indicator that provides feedback to an operator as to the state of the deployment mechanism. The indicator may be any type of indicator know in the art, for example a visual indicator, an audio indicator, or a tactile indicator. FIG. 5 shows a deployment mechanism having two indicators, a ready indicator 111 and a deployed indicator 119. Ready indicator 111 provides feedback to an operator that the deployment mechanism is in a configuration for deployment of an intraocular shunt from the deployment device 100. The indicator 111 is shown in this embodiment as a green oval having a triangle within the oval. Deployed indicator 119 provides feedback to the operator that the deployment mechanism has been fully engaged and has deployed the shunt from the deployment device 100. The deployed indicator 119 is shown in this embodiment as a yellow oval having a black square within the oval. The indicators are located on the deployment mechanism such that when assembled, the indicators 111 and 119 may be seen through slot 106 in housing 101.

Figure 6A:
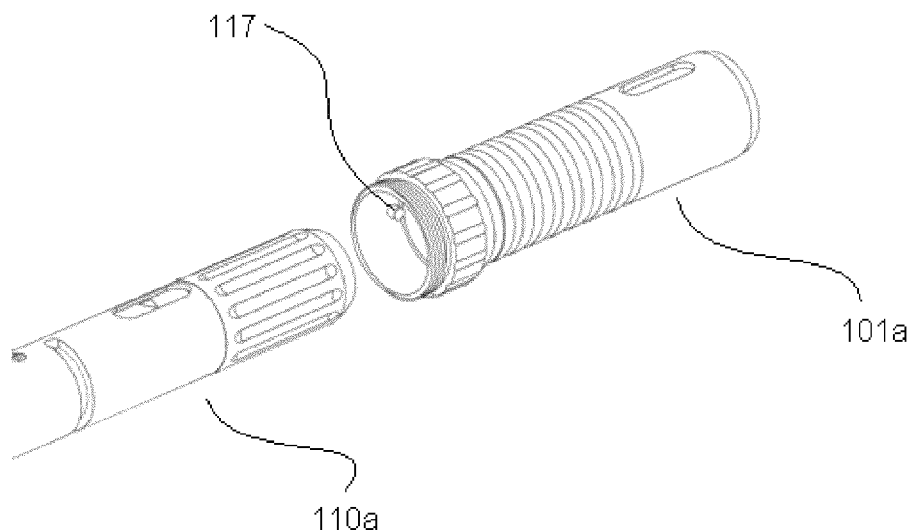
FIGS. 6A to 6C are schematics showing interaction of the deployment mechanism with a portion of the housing of the deployment device.
Figure 6B:
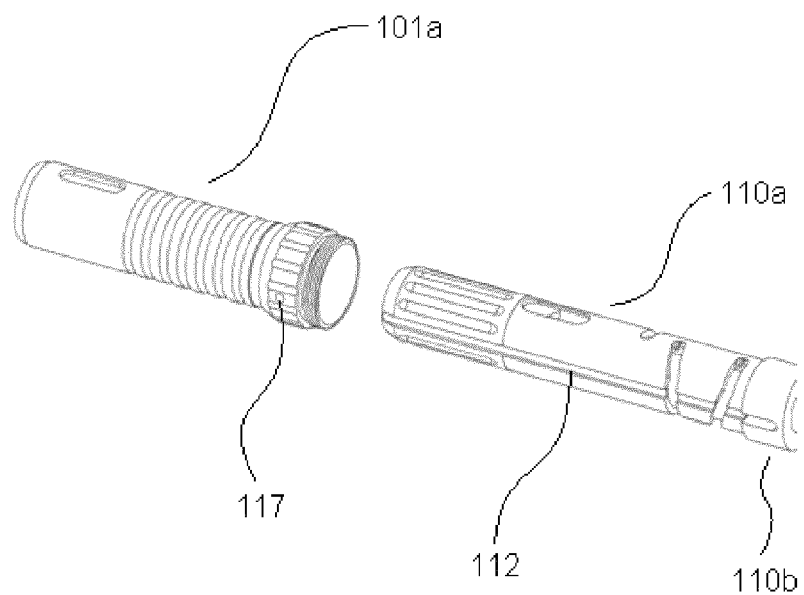
Figure 6C:
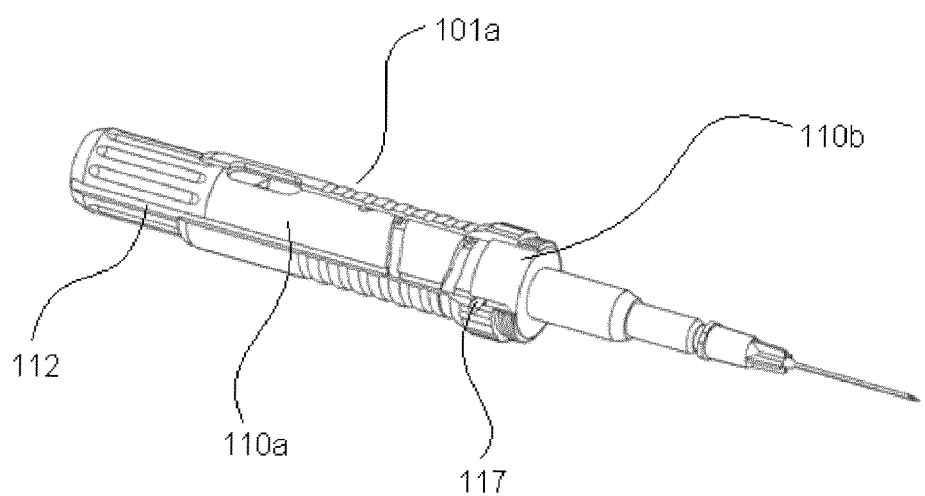

The distal portion 110 includes a stationary portion 110*b* and a rotating portion 110*a*. The distal portion 110 includes a channel 112 that runs part of the length of stationary portion 110*b* and the entire length of rotating portion 110*a*. The channel 112 is configured to interact with a protrusion 117 on an interior portion of housing component 101*a* (FIGS. 6A and 6B). During assembly, the protrusion 117 on housing component 101*a*1 is aligned with channel 112 on the stationary portion 110*b* and rotating portion 110*a* of the deployment mechanism 103. The distal portion 110 of deployment mechanism 103 is slid within housing component 101*a*1 until the protrusion 117 sits within stationary portion 110*b* (FIG. 6C). Assembled, the protrusion 117 interacts with the stationary portion 110*b* of the deployment mechanism 103 and prevents rotation of stationary portion 110*b*. In this configuration, rotating portion 110*a* is free to rotate within housing component 101*a*1.

Referring back to FIG. 5, the rotating portion 110*a* of distal portion 110 of deployment mechanism 103 also includes channels 113*a*, 113*b*, and 113*c*. Channel 113*a* includes a first portion 113*a*1 that is straight and runs perpendicular to the length of the rotating portion 110*a*, and a second portion 113*a*2 that runs diagonally along the length of rotating portion 110*a*, downwardly toward a distal end of the deployment mechanism 103. Channel 113*b* includes a first portion 113*b*1 that runs diagonally along the length of the rotating portion 110*a*, upwardly toward a proximal end of the deployment mechanism 103, and a second portion that is straight and runs perpendicular to the length of the rotating portion 110*a*. The point at which first portion 113*a*1 transitions to second portion 113*a*2 along channel 113*a*, is the same as the point at which first portion 113*b*1 transitions to second portion 113*b*2 along channel 113*b*. Channel 113*c* is straight and runs perpendicular to the length of the rotating portion 110*a*. Within each of channels 113*a*, 113*b*, and 113*c*, sit members 114*a*, 114*b*, and 114*c* respectively. Members 114*a*, 114*b*, and 114*c* are movable within channels 113*a*, 113*b*, and 113*c*. Members 114*a*, 114*b*, and 114*c* also act as stoppers that limit movement of rotating portion 110*a*, which thereby limits axial movement of the hollow shaft 104.

Figure 8:
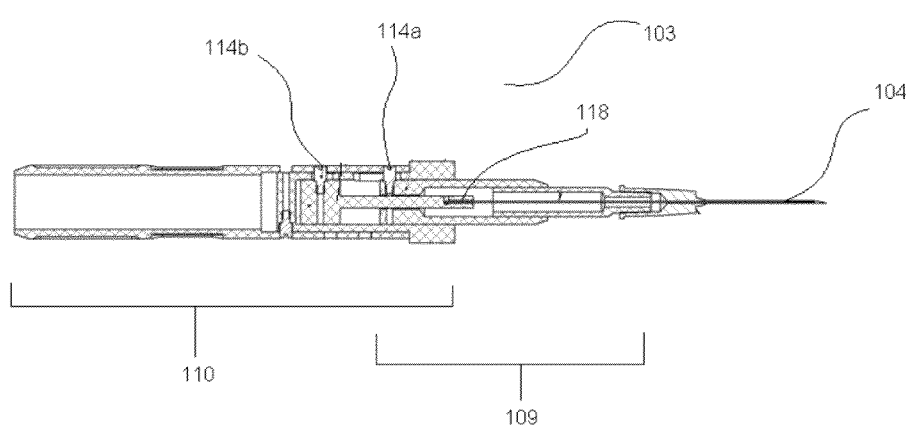
FIG. 8 shows a cross sectional view of the deployment mechanism of the deployment device.

FIG. 8 shows a cross-sectional view of deployment mechanism 103. Hollow shaft 104 is shown in this figure in its straightened configuration, as if it were housed within the outer sleeve 130. Member 114*a* is connected to the proximal portion 109 of the deployment mechanism 103. Movement of member 114*a* results in retraction of the proximal portion 109 of the deployment mechanism 103 to within the distal portion 110 of the deployment mechanism 103. Member 114*b* is connected to a pusher component 118. The pusher component 118 extends through the proximal portion 109 of the deployment mechanism 103 and extends into a portion of hollow shaft 104. The pusher component is involved in deployment of a shunt from the hollow shaft 104. An exemplary pusher component is a plunger. Movement of member 114*b* engages pusher 118 and results in pusher 118 advancing within hollow shaft 104.

Reference is now made to FIGS. 9-15, which accompany the following discussion regarding deployment of a shunt 115 from deployment device 100. FIG. 9A shows deployment device 100 in a pre-deployment or insertion configuration. In this configuration, shunt 115 is loaded within hollow shaft 104 (FIG. 9B). Hollow shaft 104 is in its straightened configuration within the outer sleeve 130. As shown in FIG. 9B, shunt 115 is fully within hollow shaft 104, such that no portion of the shunt is exposed. The shunt 115 is loaded into hollow shaft 104 such that the shunt abuts pusher component 118 within hollow shaft 104.

Figure 9A:
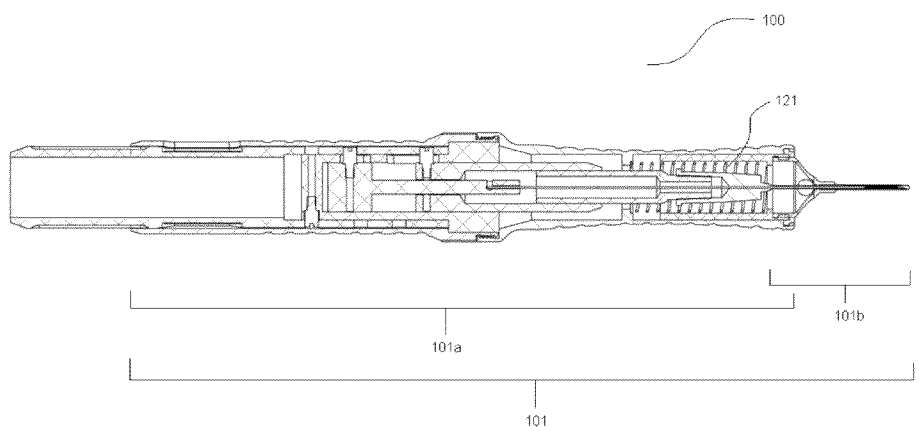
FIG. 9A is a schematic showing deployment devices of the invention in a pre-deployment or insertion configuration.
Figure 9B:
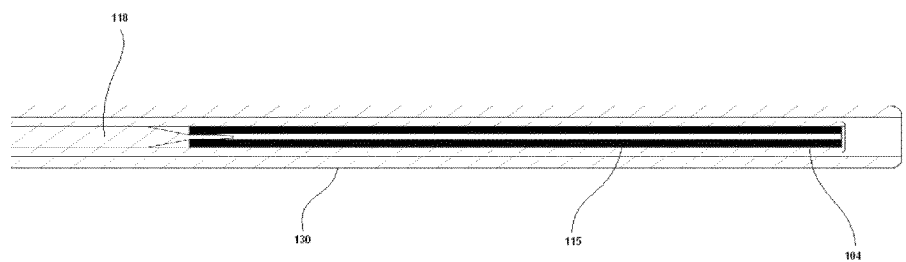
FIG. 9B shows an enlarged view of the distal portion of the deployment device of FIG. 9A. This figure shows an intraocular shunt loaded within a hollow shaft of the deployment device and that the shaft is completely disposed within the sleeve of the housing. In this configuration, the hollow shaft is straight.

In the pre-deployment or insertion configuration, the distal portion 101*b* of the housing 101 is in an extended position, with spring 121 in a relaxed state (FIG. 9A). Additionally, in the pre-deployment configuration, the hollow shaft 104 is fully disposed within the sleeve 130 of the distal portion 101*b* of the housing 101 (FIG. 9B). Pusher 118 abuts shunt 115 (FIG. 9B).

Figure 9C:
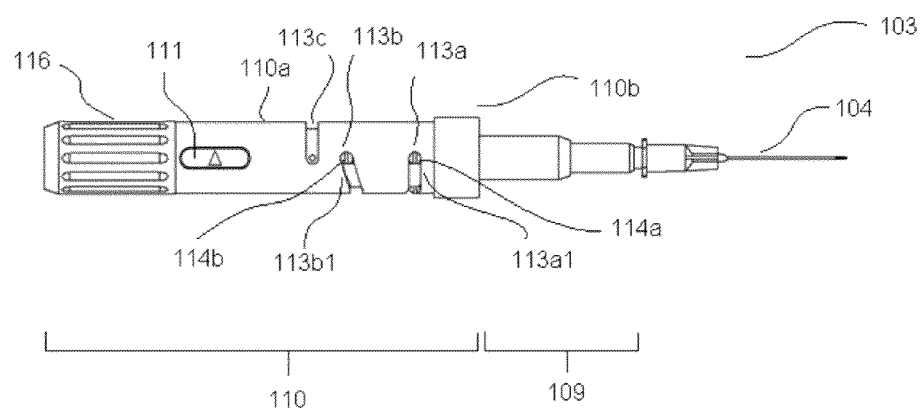
FIG. 9C show a schematic of the deployment mechanism in a pre-deployment or insertion configuration.
Figure 9D:
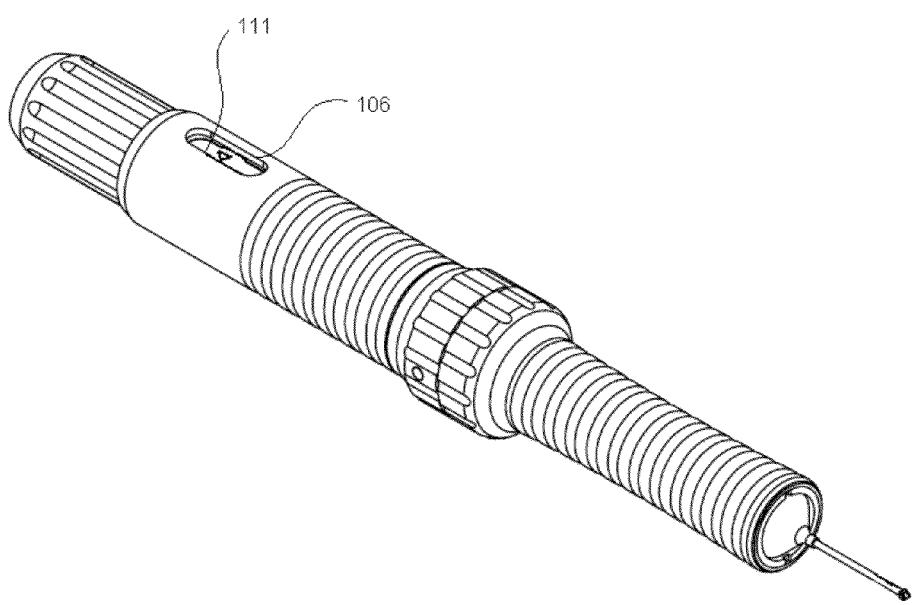
FIG. 9D is another schematic showing deployment devices of the invention in a pre-deployment or insertion configuration.

The deployment mechanism 103 is configured such that member 114*a* abuts a proximal end of the first portion 113*a*1 of channel 113*a*, and member 114*b* abut a proximal end of the first portion 113*b*1 of channel 113*b* (FIG. 9C). Hollow shaft 104 is shown in this figure in its straightened configuration, as if it were housed within the outer sleeve 130. In this configuration, the ready indicator 111 is visible through slot 106 of the housing 101, providing feedback to an operator that the deployment mechanism is in a configuration for deployment of an intraocular shunt from the deployment device 100 (FIG. 9D). In this configuration, the device 100 is ready for insertion into an eye (insertion configuration or pre-deployment configuration).

Figure 10A:
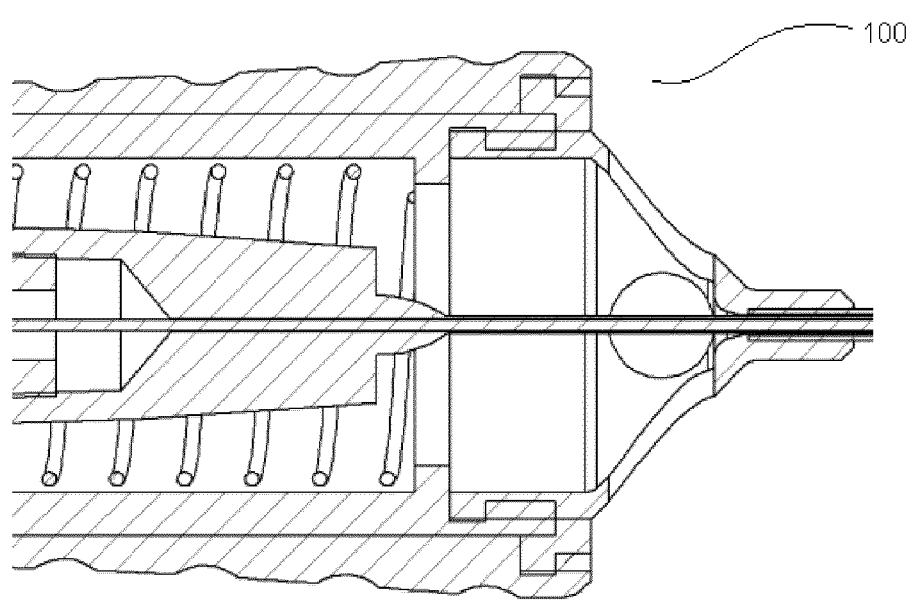
FIGS. 10A-B are schematics showing insertion of a device of the invention into an anterior chamber of the eye.
Figure 10B:
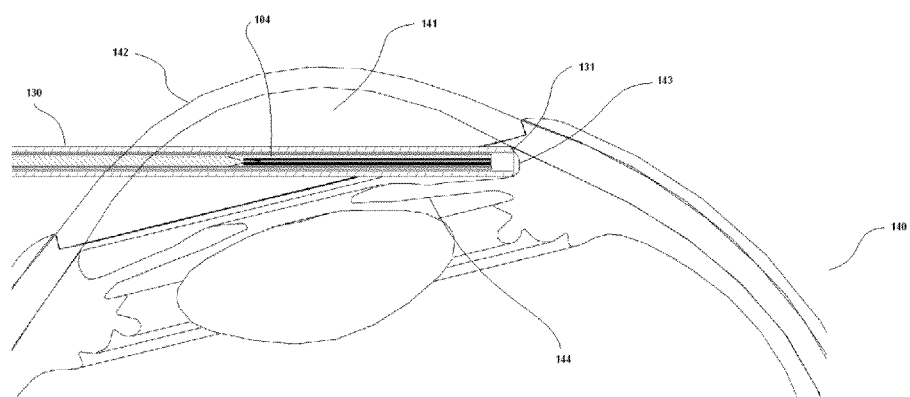

FIGS. 10A-B show device 100 in the insertion configuration and inserted into an eye 140. FIG. 10A is a magnified view of the position of the distal portion 101b relative to the proximal portion 101a in the insertion configuration. FIG. 10B is a magnified view of the sleeve 130 of device 100 inserted into the eye. Any of a variety of methods known in the art may be used to insert devices of the invention into an eye. In certain embodiments, devices of the invention may be inserted into the eye using an ab externo approach (entering through the conjunctiva) or an ab interno approach (entering through the cornea). In particular embodiment, the approach is an ab interno approach as shown Yu et al. (U.S. Pat. No. 6,544,249 and U.S. patent application number 2008/0108933) and Prywes (U.S. Pat. No. 6,007,511), the content of each of which is incorporated by reference herein in its entirety.

FIGS. 10A-B shows an ab interno approach for insertion of device 100 into the eye 140. In FIG. 10B, protrusion 131 at the distal end of the sleeve 130 has been advanced across the anterior chamber 141 to the sclera 142 on the opposite side of the eye 140 from which the device entered the eye 140. FIG. 10B shows protrusion 131 and sleeve 130 fitted within the anterior chamber angle 143 of the eye 140. Such insertion and placement is accomplished without the use of an optical apparatus that contacts the eye, such as a goniolens. In certain embodiments this insertion is accomplished without the use of any optical apparatus.

Insertion without the use of an optical apparatus that contacts the eye, or any optical apparatus, is possible because of various features of the device described above and reviewed here briefly. The shape of the protrusion 131 is such that it corrects for an insertion angle that is too steep or too shallow, ensuring that the sleeve 130 is fitted into the anterior chamber angle of the eye, the place for proper deployment of an intraocular shunt. Further, the shape of the protrusion provides adequate surface area at the distal end of sleeve 130 to prevent enough force from being generated at the distal end of sleeve 130 that would result in sleeve 130 entering an improper portion of the sclera 142 (if the insertion angle is too shallow) or entering an improper portion of the iris 144 (if the insertion angle is too steep). Additionally, since the hollow shaft 104 is fully disposed within the sleeve 130, it cannot pierce tissue of the eye until it is extended from the sleeve 130. Thus, if the insertion angle is too shallow or too steep, the protrusion 131 can cause movement and repositioning of the sleeve 130 so that the sleeve 130 is properly positioned to fit in the anterior chamber angle of the eye for proper deployment of the shunt. Due to these features of device 100, devices of the invention provide for deploying intraocular shunts without use of an optical apparatus that contacts the eye, preferably without use of any optical apparatus.

Figure 11A:
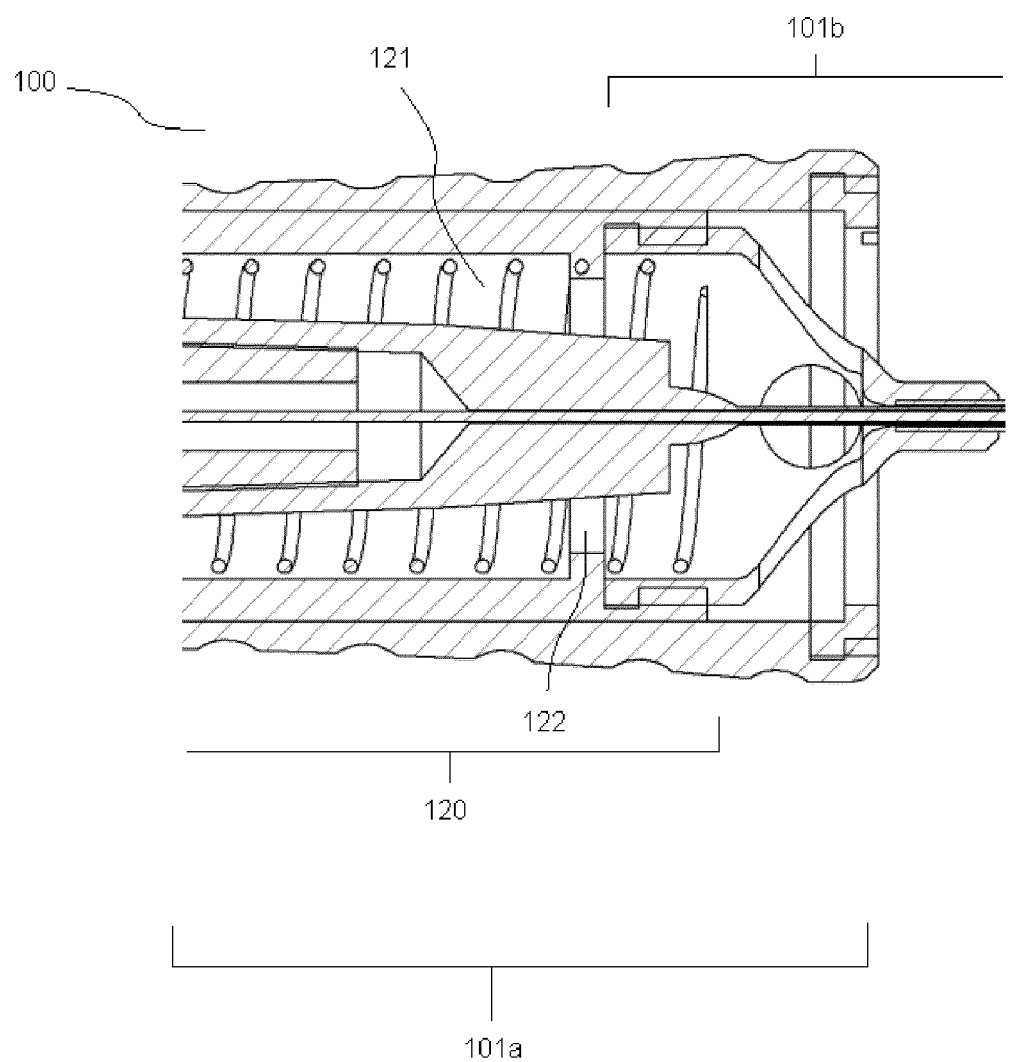
FIGS. 11A-B are schematics showing extension of the shaft from within the sleeve, which is accomplished by partial retraction of the distal portion of housing to within the proximal portion of housing.
Figure 11B:
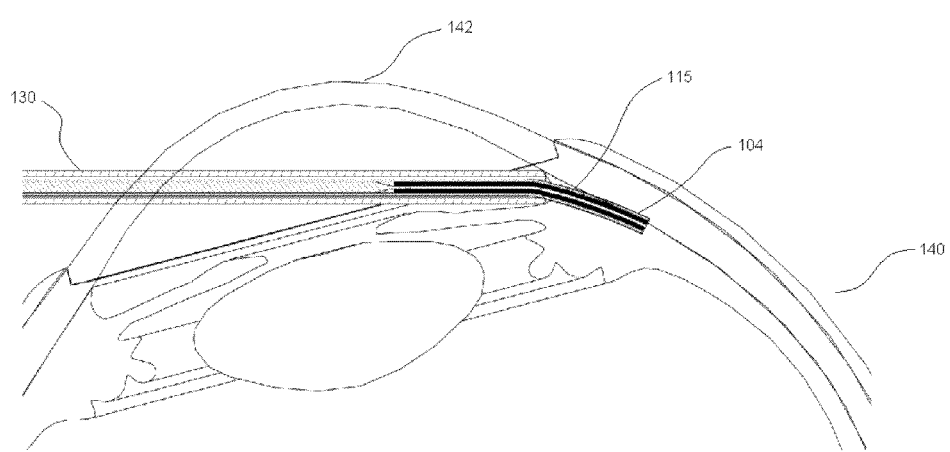

Once the device has been inserted into the eye and the protrusion 131 and the sleeve 130 are fitted within the anterior chamber angle of the eye, the hollow shaft 104 may be extended from within the sleeve 130. Referring now to FIGS. 11A-B which show extension of the hollow shaft 104 from within the sleeve 130, which is accomplished by partial retraction of distal portion 101b of housing 101 to within proximal portion 101a of housing 101 (FIG. 11A).

Retraction of the distal portion 101b of housing 101 to within proximal portion 101a of housing 101 is accomplished by an operator continuing to apply force to advance device 100 after the protrusion 131 and the sleeve 130 are fitted within the anterior chamber angle of the eye. The surface area of protrusion 131 prevents the application of the additional force by the operator from advancing sleeve 130 into the sclera 134. Rather, the additional force applied by the operator results in engagement of spring mechanism 120 and compression of spring 121 within spring mechanism 120. Compression of spring 120 results in retraction of distal portion 101b of housing 101 to within proximal portion 101a of housing 101. The amount of retraction of distal portion 101b of housing 101 to within proximal portion 101a of housing 101 is limited by member 122 that acts as a stopper and limits axial retraction of distal portion 101b within proximal portion 101a.

Retraction of distal portion 101b of housing 101 to within proximal portion 101a of housing 101 results in extension of hollow shaft 104, which now extends beyond the distal end of sleeve 130 and advances through the sclera 142 (FIG. 11B). The rigidity of the sleeve 130 holds hollow shaft 104 in a straight configuration. Upon its exposure from the sleeve 130, hollow shaft 104 reverts to its pre-bent configuration, which bend minors the angle or arc of the sclera. Such a pre-bend allows the hollow shaft 104 to follow the scleral spur down along the sclera in a self-guided manner to the suprachoroidal space. Generally, the bend in the hollow shaft 104 will be from about 5° degrees to about 70° degrees.

Additionally, the flexibility of the hollow shaft 104 allows it to continually bend and flex in response to the anatomy as the hollow shaft 104 advances from the sleeve 130. The hollow shaft 104 is advanced until a distal portion of the hollow shaft 104 is within the suprachoroidal space. In this configuration, the shunt 115 is still completely disposed within the shaft 104. The distal end of hollow shaft 104 may be beveled to assist in piercing the sclera and advancing the distal end of the hollow shaft 104 through the sclera.

At this point, an amount of BSS/steroid or other drug can be optionally injected through the hollow shaft and implant into a lower end of the target space to create a primed space for outflow and to deliver antifibrotic or other drugs to that new drainage space.

Figure 12A:
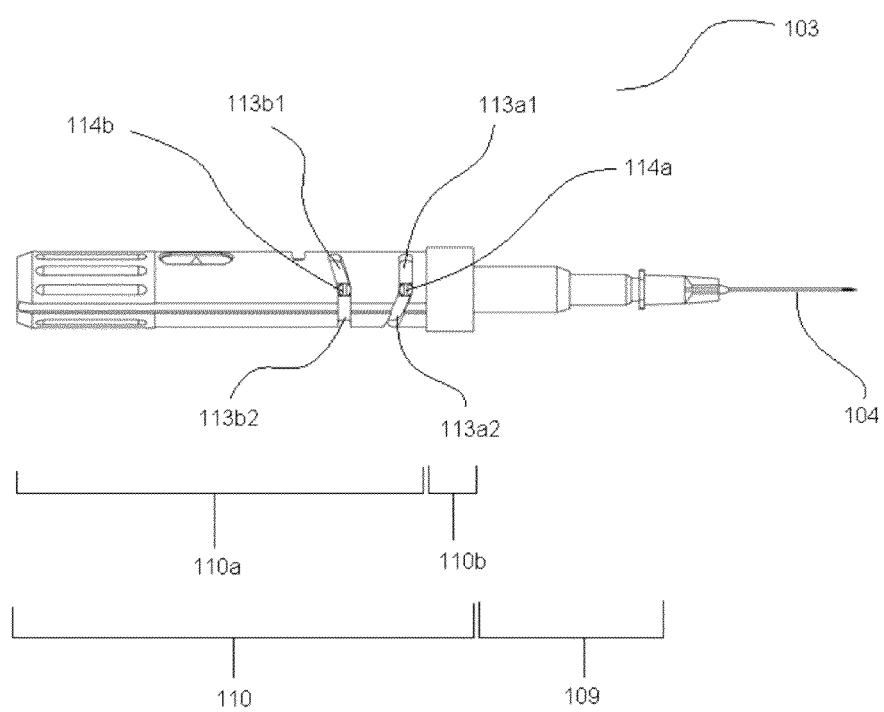
FIGS. 12A-B show schematics of the deployment mechanism at the end of the first stage of deployment of the shunt from the deployment device.
Figure 12B:
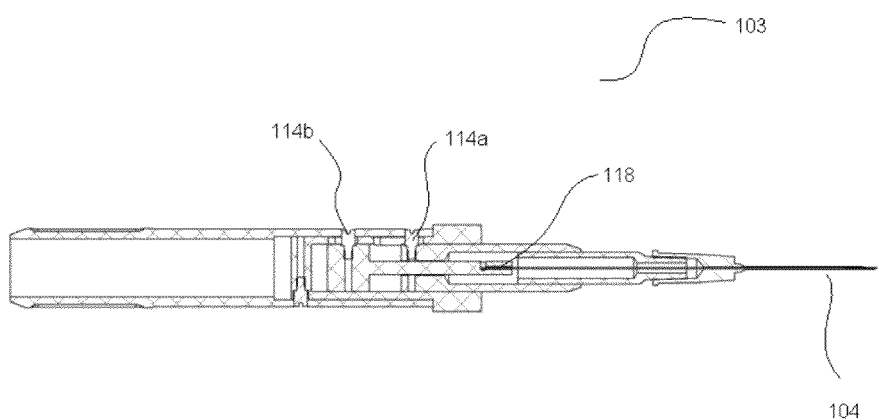
Figure 12C:
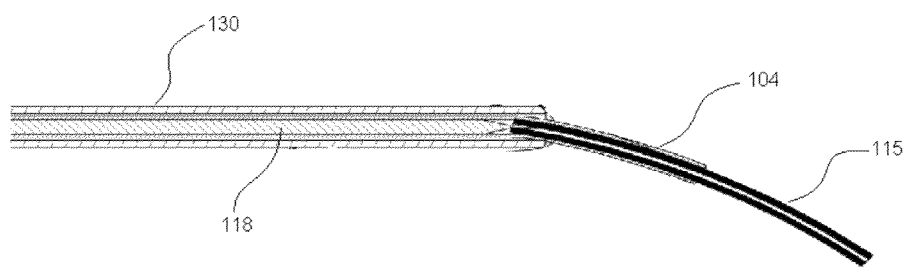
FIG. 12C shows an enlarged view of the distal portion of the deployment device of FIG. 12A. In this figure, the shaft is shown exposed from the sleeve and in its bent configuration This figure shows an intraocular shunt partially deployed from within a hollow shaft of the deployment device.

Reference is now made to FIGS. 12A-C. After extension of hollow shaft 104 from sleeve 130, the shunt 115 may be deployed from the device 100. The deployment mechanism 103 is a two-stage system. The first stage is engagement of the pusher component 118 and the second stage is retraction of the proximal portion 109 of deployment mechanism 103 to within the distal portion 110 of the deployment mechanism 103. Rotation of the rotating portion 110a of the distal portion 110 of the deployment mechanism 103 sequentially engages the pusher component and then the retraction component.

In the first stage of shunt deployment, the pusher component is engaged and the pusher partially deploys the shunt from the deployment device. During the first stage, rotating portion 110a of the distal portion 110 of the deployment mechanism 103 is rotated, resulting in movement of members 114a and 114b along first portions 113a1 and 113b1 in channels 113a and 113b. Since the first portion 113a1 of channel 113a is straight and runs perpendicular to the length of the rotating portion 110a, rotation of rotating portion 110a does not cause axial movement of member 114a. Without axial movement of member 114a, there is no retraction of the proximal portion 109 to within the distal portion 110 of the deployment mechanism 103. Since the first portion 113b1 of channel 113b runs diagonally along the length of the rotating portion 110a, upwardly toward a proximal end of the deployment mechanism 103, rotation of rotating portion 110a causes axial movement of member 114b toward a proximal end of the device. Axial movement of member 114b toward a proximal end of the device results in forward advancement of the pusher component 118 within the hollow shaft 104. Such movement of pusher component 118 results in partially deployment of the shunt 115 from the hollow shaft 104.

FIGS. 12A-C show schematics of the deployment mechanism at the end of the first stage of deployment of the shunt from the deployment device. FIGS. 12A-B show the shaft in a straight configuration, as if it is within the stiff outer sleeve. As is shown FIG. 12A, members 114a and 114b have finished traversing along first portions 113a1 and 113b1 of channels 113a and 113b. Additionally, pusher component 118 has advanced within hollow shaft 104 (FIG. 12B), and shunt 115 has been partially deployed from the hollow shaft 104 (FIG. 12C). As is shown in FIG. 12C, a portion of the shunt 115 extends beyond an end of the hollow shaft 104.

Figure 13A:
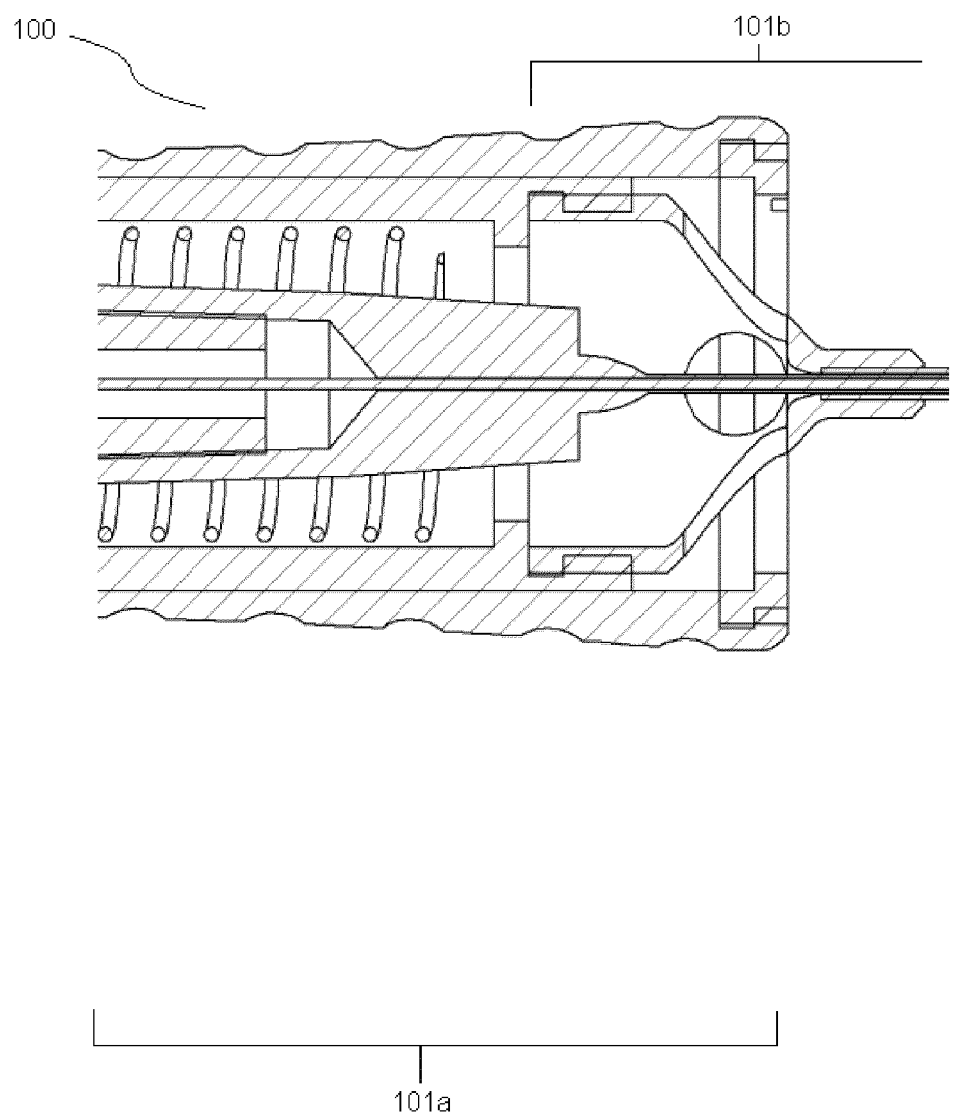
FIG. 13A-B are schematics showing the deployment device after completion of the first stage of deployment of the shunt from the device and in to the eye.
Figure 13B:
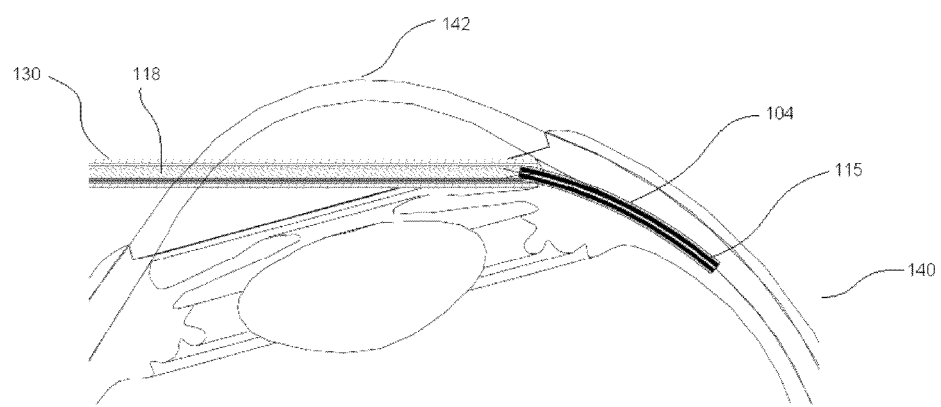

FIGS. 13A-B show device 100 at the end of the first stage of deployment of the shunt 115 from device 100 and into the eye 140. This figure shows that the distal portion 101b of the housing 101 remains retracted within the proximal portion 101a of the housing 101, and that the hollow shaft 104 remains extended from the sleeve 130. As is shown in these figures, pusher 118 has been engaged, which allows for shunt 115 to be deployed from hollow shaft 104.

Reference is now made to FIGS. 14A-D. In the second stage of shunt deployment, the retraction component of deployment mechanism is engaged and the proximal portion of the deployment mechanism is retracted to within the distal portion of the deployment mechanism, thereby completing deployment of the shunt from the deployment device. During the second stage, rotating portion 110a of the distal portion 110 of the deployment mechanism 103 is further rotated, resulting in movement of members 114a and 114b along second portions 113a2 and 113b2 in channels 113a and 113b. Since the second portion 113b2 of channel 113b is straight and runs perpendicular to the length of the rotating portion 110a, rotation of rotating portion 110a does not cause axial movement of member 114b. Without axial movement of member 114b, there is no further advancement of pusher 118. Since the second portion 113a2 of channel 113a runs diagonally along the length of the rotating portion 110a, downwardly toward a distal end of the deployment mechanism 103, rotation of rotating portion 110a causes axial movement of member 114a toward a distal end of the device. Axial movement of member 114a toward a distal end of the device results in retraction of the proximal portion 109 to within the distal portion 110 of the deployment mechanism 103. Retraction of the proximal portion 109, results in retraction of the hollow shaft 104. Since the shunt 115 abuts the pusher component 118, the shunt remains stationary at the hollow shaft 104 retracts from around the shunt 115. The hollow shaft 104, retracts completely to within the sleeve 130 of the distal portion 101b of the housing 101. During both stages of the deployment process, the housing 101 remains stationary and in a fixed position.

Figure 14A:
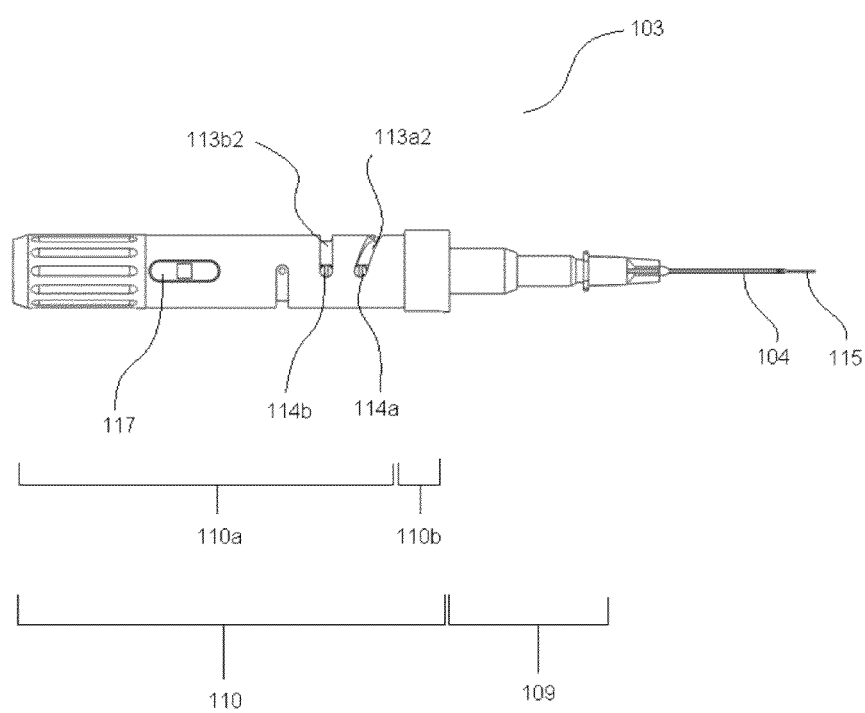
FIG. 14A show a schematic of the deployment mechanism at the end of the second stage of deployment.

Referring to FIG. 14A, which shows a schematic of the deployment mechanism at the end of the second stage of deployment of the shunt from the deployment device. As is shown in FIG. 14A, members 114a and 114b have finished traversing along second portions 113a1 and 113b1 of channels 113a and 113b. Additionally, proximal portion 109 has retracted to within distal portion 110, thus resulting in retraction of the hollow shaft 104 to within the housing 101. FIG. 14A shows the shaft in a straight configuration, after it has been retracted into the stiff outer sleeve.

Figure 14B:
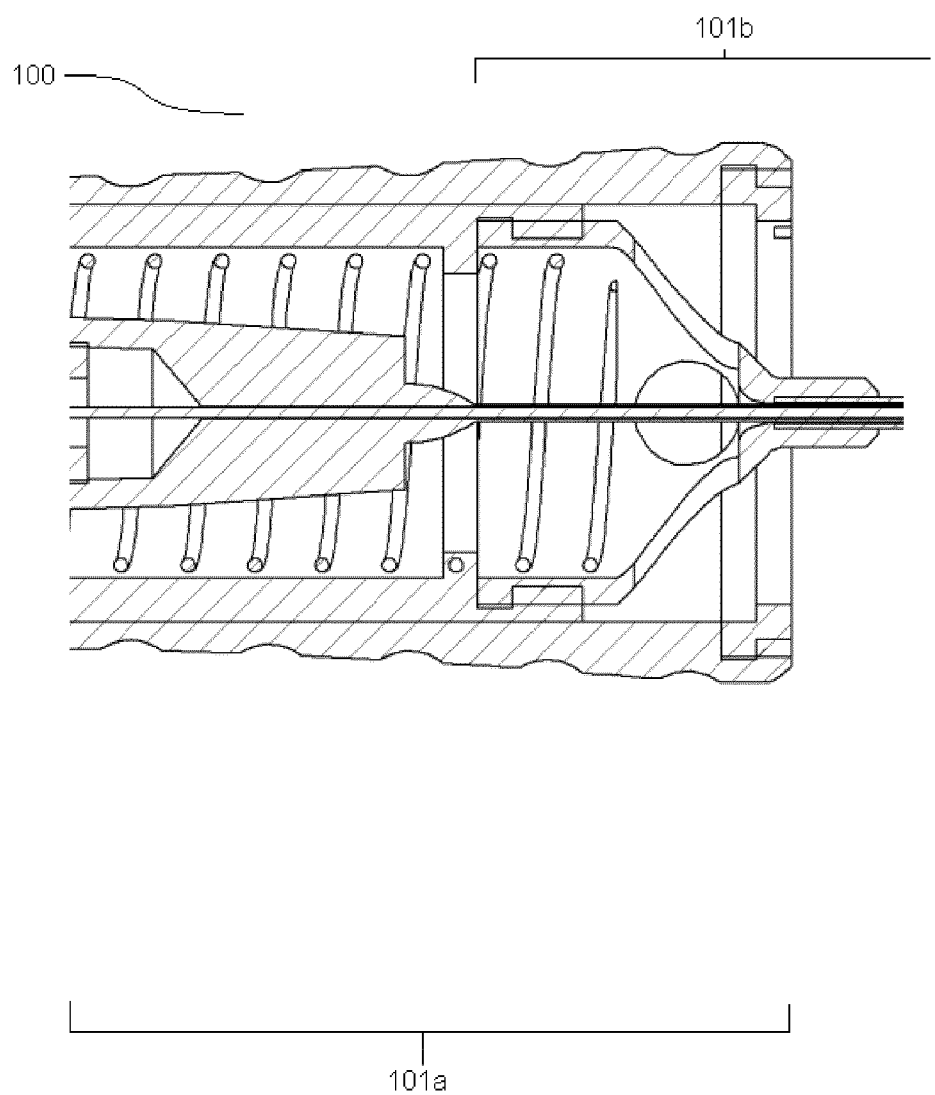
FIGS. 14B-C show schematics of the deployment device during the second stage of deployment.
Figure 14C:
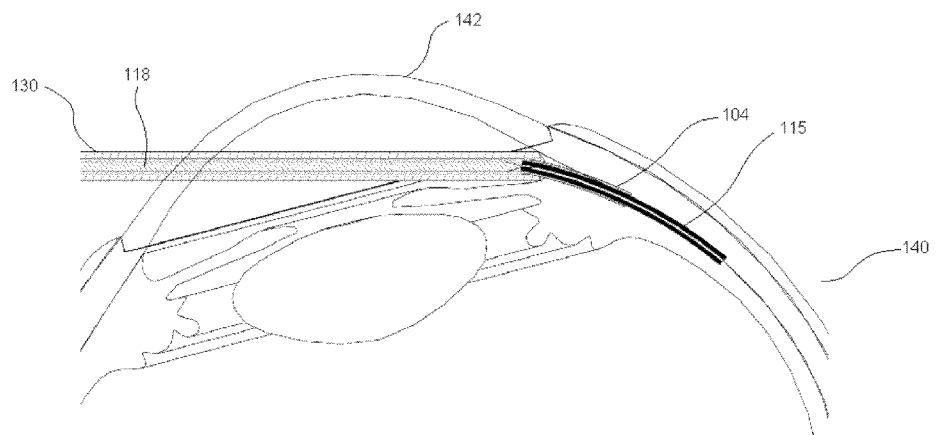

FIGS. 14B-C show schematics of the device 100 in the eye 130 during the second stage of deployment. FIG. 14B shows that the distal portion 101b of the housing 101 remains retracted within the proximal portion 101a of the housing 101. As is shown in FIG. 14C, hollow shaft 104 is withdrawing through the sclera 134 and is retracting to within sleeve 130. This action continues through the second stage of deployment until the hollow shaft 104 is fully retracted to within sleeve 130.

Figure 14D:
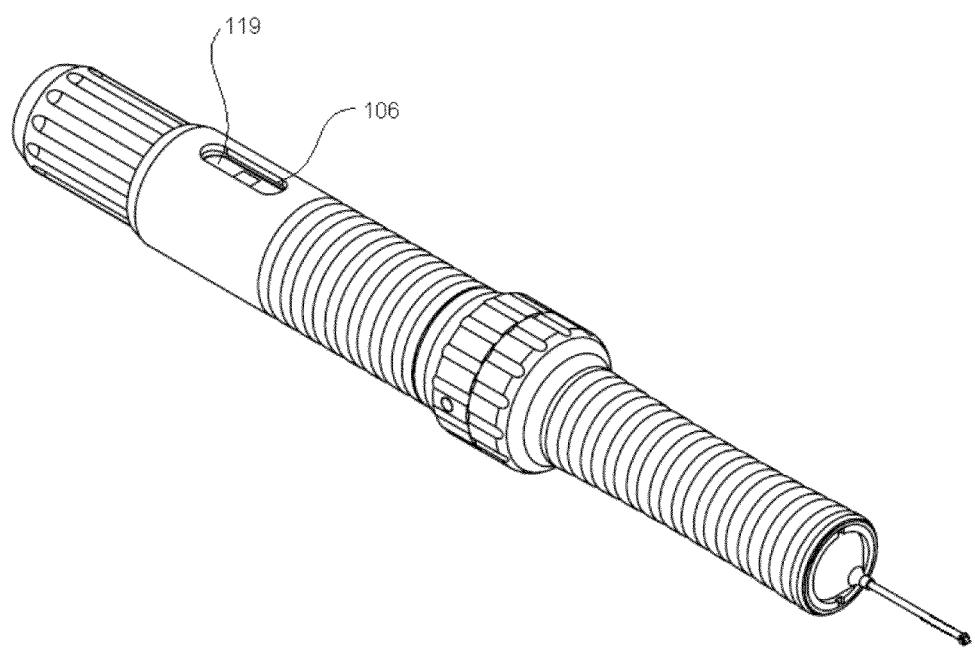
FIG. 14D shows another view of the deployment device at the end of the second stage of deployment.

Referring to FIG. 14D, in the post-deployment configuration, the deployed indicator 119 is visible through slot 106 of the housing 101, providing feedback to the operator that the deployment mechanism 103 has been fully engaged and that the deployment mechanism 103 has completed its second stage of deployment.

Figure 15A:
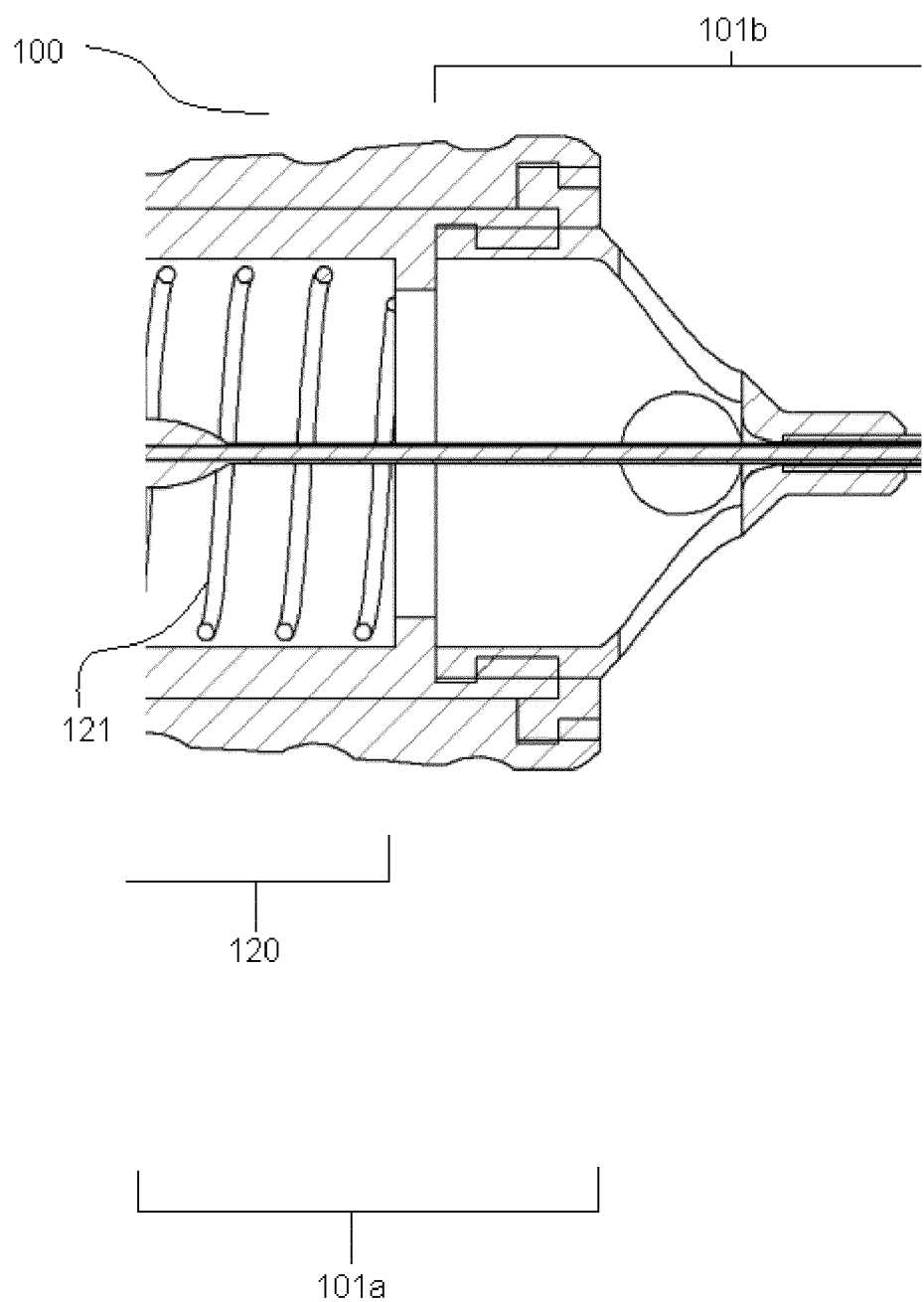
FIGS. 15A-B are schematics showing the deployment device after completion of deployment of the shunt from the device and in to the eye.
Figure 15B:
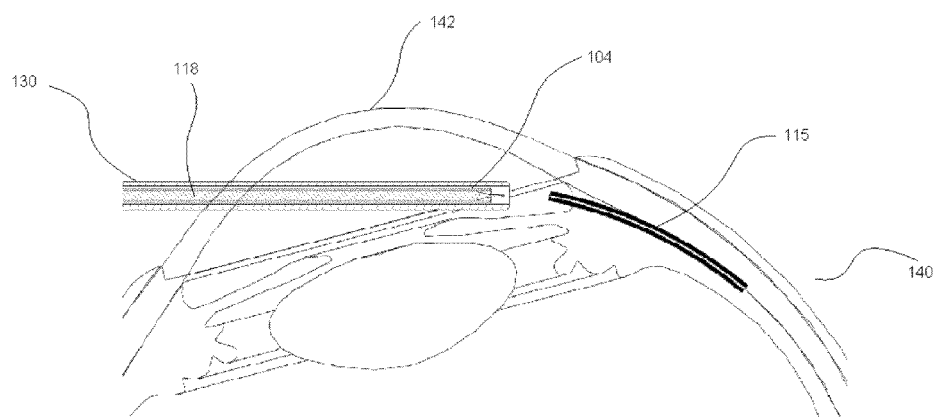

Referring to FIGS. 15A-B, which show schematics of the device 100 after completion of deployment of the shunt 115 from the device 100 and in to the eye 140. After completion of the second stage of the deployment by the deployment mechanism 103, as indicated to the operator by visualization of deployed indicator 119 through slot 106 of the housing 101, the operator may pull the device 100 from the eye 140. Backward force by the operator reengages spring mechanism 120 and results in uncoiling of spring 121 (FIG. 15A). Uncoiling of spring 121 proceeds as the proximal portion 101a of housing 101 is pulled from the eye 140. Such action causes distal portion 101b to return to its extended state within proximal portion 101a of housing 101 (FIG. 15A). Continued backward force by the operator continues to pull the device 100 from the eye 140. As the device 100 is continued to be pulled from the eye, the sleeve 130 is also pulled backward and the proximal portion of the shunt 115 is exposed from within the sleeve 130 and resides within the anterior chamber 141 of the eye 140 (FIG. 15B). The operator continues to apply backward force until the device 100 is completely withdrawn from the eye 140. At this point, a distal portion of the shunt 115 has been deployed and resides in the suprachoroidal space, a middle portion of the shunt 115 spans the sclera, and a proximal portion of shunt 115 has been deployed and resides in the anterior chamber.

Three Stage Deployment Mechanism

Another embodiment by which the hollow shaft 104 may be extended from the sleeve 130 involves a deployment mechanism that is a three-stage mechanism. The three-stage mechanism operates similarly to the above described device that uses a spring loaded distal portion and a two-stage deployment mechanism. In the three-stage system, the channels of the deployment mechanism are extended to accommodate the new first stage. The newly added portion of the channels run diagonally upward along the length of the rotating portion toward the proximal end of the deployment mechanism. Axial movement by the members within the channels results in the extension of the hollow shaft 104 from the sleeve 130. The new first stage replaces the spring loaded distal portion and results in extension of the hollow shaft 104 from the sleeve 130. The engagement of the pusher component 118 becomes the second stage and retraction of the proximal portion 109 of deployment mechanism 103 to within the distal portion 110 of the deployment mechanism 103 becomes the third stage. The second and third stages of the three-stage system are the same as the first and second stages of the two-stage system and operate as described above. Rotation of the rotating portion of the distal portion of the deployment mechanism sequentially extends the hollow shaft from the sleeve, engages the pusher component and then engages the retraction component.

Intraocular Shunts of the Invention

The present invention provides intraocular shunts that are configured to form a drainage pathway from the anterior chamber of the eye to the suprachoroidal space. Shunts of the invention may be any length that allows for drainage of aqueous humor from an anterior chamber of an eye to the suprachoroidal space. Exemplary shunts range in length from approximately 2 mm to approximately 20 mm or between approximately 4 mm to approximately 15 mm, or any specific value within said ranges. In certain embodiments, the length of the shunt is any length between approximately 10 to 15 mm, or any specific value within said range, e.g., 10 mm, 10.5 mm, 11 mm, 11.5 mm, 12 mm, 12.5 mm, 13 mm, 13.5 mm, 14 mm, 14.5 mm, or 15 mm.

The intraocular shunts of the invention are particularly suitable for use in an ab interno glaucoma filtration procedure. In particular embodiments, the intraocular shunts of the invention are flexible, and have an elasticity modulus that is substantially identical to the elasticity modulus of the surrounding tissue in the implant site. As such, the intraocular shunts of the invention are easily bendable, do not erode or cause a tissue reaction, and do not migrate once implanted. Thus, when implanted in the eye using an ab interno procedure, such as the methods described herein, the intraocular shunts of the invention do not induce substantial ocular inflammation such as subconjunctival blebbing or endophthalmitis. Additional exemplary features of the intraocular shunts of the invention are discussed in further detail below.

Tissue Compatible Shunts

In certain aspects, the invention generally provides shunts composed of a material that has an elasticity modulus that is compatible with an elasticity modulus of tissue surrounding the shunt (e.g., tissue surrounding the suprachoroidal space). In this manner, shunts of the invention are flexibility matched with the surrounding tissue, and thus will remain in place after implantation without the need for any type of anchor that interacts with the surrounding tissue. Consequently, shunts of the invention will maintain fluid flow away for an anterior chamber of the eye after implantation without causing irritation or inflammation to the tissue surrounding the eye.

Elastic modulus, or modulus of elasticity, is a mathematical description of an object or substance's tendency to be deformed elastically when a force is applied to it. The elastic modulus of an object is defined as the slope of its stress-strain curve in the elastic deformation region:

$$\lambda \stackrel{def}{=} \frac{stress}{strain}$$

where lambda ($\lambda$) is the elastic modulus; stress is the force causing the deformation divided by the area to which the force is applied; and strain is the ratio of the change caused by the stress to the original state of the object. The elasticity modulus may also be known as Young's modulus (E), which describes tensile elasticity, or the tendency of an object to deform along an axis when opposing forces are applied along that axis. Young's modulus is defined as the ratio of tensile stress to tensile strain. For further description regarding elasticity modulus and Young's modulus, see for example Gere (Mechanics of Materials, 6$^{th}$ Edition, 2004, Thomson), the content of which is incorporated by reference herein in its entirety.

The elasticity modulus of any tissue can be determined by one of skill in the art. See for example Samani et al. (Phys. Med. Biol. 48:2183, 2003); Erkamp et al. (Measuring The Elastic Modulus Of Small Tissue Samples, Biomedical Engineering Department and Electrical Engineering and Computer Science Department University of Michigan Ann Arbor, Mich. 48109-2125; and Institute of Mathematical Problems in Biology Russian Academy of Sciences, Pushchino, Moscow Region 142292 Russia); Chen et al. (IEEE Trans. Ultrason. Ferroelec. Freq. Control 43:191-194, 1996); Hall, (In 1996 Ultrasonics Symposium Proc., pp. 1193-1196, IEEE Cat. No. 96CH35993, IEEE, New York, 1996); and Parker (Ultrasound Med. Biol. 16:241-246, 1990), each of which provides methods of determining the elasticity modulus of body tissues. The content of each of these is incorporated by reference herein in its entirety.

The elasticity modulus of tissues of different organs is known in the art. For example, Pierscionek et al. (Br J Ophthalmol, 91:801-803, 2007) and Friberg (Experimental Eye Research, 473:429-436, 1988) show the elasticity modulus of the cornea and the sclera of the eye. The content of each of these references is incorporated by reference herein in its entirety. Chen, Hall, and Parker show the elasticity modulus of different muscles and the liver. Erkamp shows the elasticity modulus of the kidney.

Shunts of the invention are composed of a material that is compatible with an elasticity modulus of tissue surrounding the shunt. In certain embodiments, the material has an elasticity modulus that is substantially identical to the elasticity modulus of the tissue surrounding the shunt. In other embodiments, the material has an elasticity modulus that is greater than the elasticity modulus of the tissue surrounding the shunt. Exemplary materials includes biocompatible polymers, such as polycarbonate, polyethylene, polyethylene terephthalate, polyimide, polystyrene, polypropylene, poly(styrene-b-isobutylene-b-styrene), or silicone rubber.

In particular embodiments, shunts of the invention are composed of a material that has an elasticity modulus that is compatible with the elasticity modulus of tissue in the eye, particularly scleral tissue. In certain embodiments, compatible materials are those materials that are softer than scleral tissue or marginally harder than scleral tissue, yet soft enough to prohibit shunt migration. The elasticity modulus for anterior scleral tissue is approximately $2.9\pm1.4\times10^6$ N/m$^2$, and $1.8\pm1.1\times10^6$ N/m$^2$ for posterior scleral tissue. See Friberg (Experimental Eye Research, 473:429-436, 1988). An exemplary material is cross linked gelatin derived from Bovine or Porcine Collagen.

The invention encompasses shunts of different shapes and different dimensions, and the shunts of the invention may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm.

Shunts Reactive to Pressure

Figure 16:
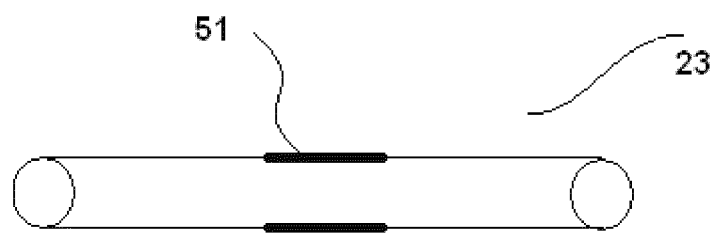

In other aspects, the invention generally provides shunts in which a portion of the shunt is composed of a flexible material that is reactive to pressure, i.e., the diameter of the flexible portion of the shunt fluctuates depending upon the pressures exerted on that portion of the shunt. FIG. 16 provides a schematic of a shunt 23 having a flexible portion 51 (thicker black lines). In this figure, the flexible portion 51 is shown in the middle of the shunt 23. However, the flexible portion 51 may be located in any portion of the shunt, such as the proximal or distal portion of the shunt. In certain embodiments, the entire shunt is composed of the flexible material, and thus the entire shunt is flexible and reactive to pressure.

The flexible portion 51 of the shunt 23 acts as a valve that regulates fluid flow through the shunt. The human eye produces aqueous humor at a rate of about 2 μl/min for approximately 3 ml/day. The entire aqueous volume is about 0.25 ml. When the pressure in the anterior chamber falls after surgery to about 7-8 mmHg, it is assumed the majority of the aqueous humor is exiting the eye through the implant since venous backpressure prevents any significant outflow through normal drainage structures (e.g., the trabecular meshwork).

After implantation, intraocular shunts have pressure exerted upon them by tissues surrounding the shunt (e.g., scleral tissue such as the sclera channel and the sclera exit) and pressure exerted upon them by aqueous humor flowing through the shunt. The flow through the shunt, and thus the pressure exerted by the fluid on the shunt, is calculated by the equation:

$$\Phi = \frac{dV}{dt} = v\pi R^2 = \frac{\pi R^4}{8\eta}\left(\frac{-\Delta P}{\Delta x}\right) = \frac{\pi R^4}{8\eta}\frac{|\Delta P|}{L}$$

where $\Phi$ is the volumetric flow rate; V is a volume of the liquid poured (cubic meters); t is the time (seconds); v is mean fluid velocity along the length of the tube (meters/second); x is a distance in direction of flow (meters); R is the internal radius of the tube (meters); $\Delta P$ is the pressure difference between the two ends (pascals); $\eta$ is the dynamic fluid viscosity (pascal-second (Pa·s)); and L is the total length of the tube in the x direction (meters).

Figure 17A:
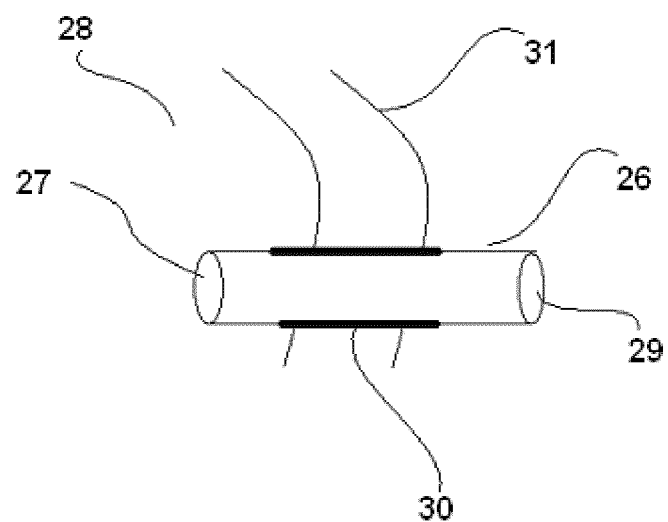
FIGS. 17A, 17B and 17C provide schematics of a shunt implanted into an eye for regulation of fluid flow from the anterior chamber of the eye to a drainage structure of the eye.

FIG. 17A provides a schematic of a shunt 26 implanted into an eye for regulation of fluid flow from the anterior chamber of the eye to an area of lower pressure (e.g., the intra-scleral space). The shunt is implanted such that a proximal end 27 of the shunt 26 resides in the anterior chamber 28 of the eye, and a distal end 29 of the shunt 26 resides outside of the anterior chamber to conduct aqueous humor from the anterior chamber to an area of lower pressure. A flexible portion 30 (thicker black lines) of the shunt 26 spans at least a portion of the sclera of the eye. As shown in FIG. 17A, the flexible portion spans an entire length of the sclera 31.

Figure 17B:
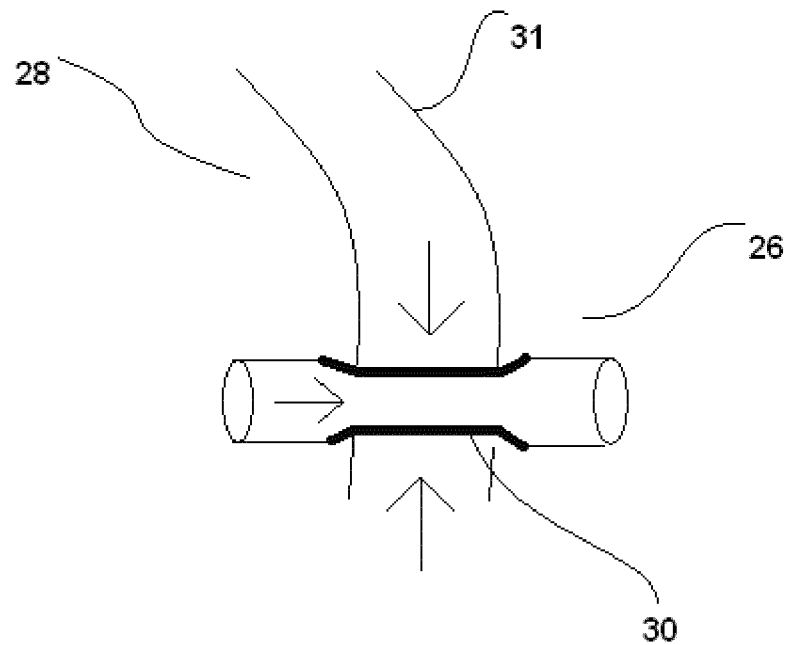

When the pressure exerted on the flexible portion 30 of the shunt 26 by sclera 31 (vertical arrows) is greater than the pressure exerted on the flexible portion 30 of the shunt 26 by the fluid flowing through the shunt (horizontal arrow), the flexible portion 30 decreases in diameter, restricting flow through the shunt 26 (FIG. 17B). The restricted flow results in aqueous humor leaving the anterior chamber 28 at a reduced rate.

Figure 17C:
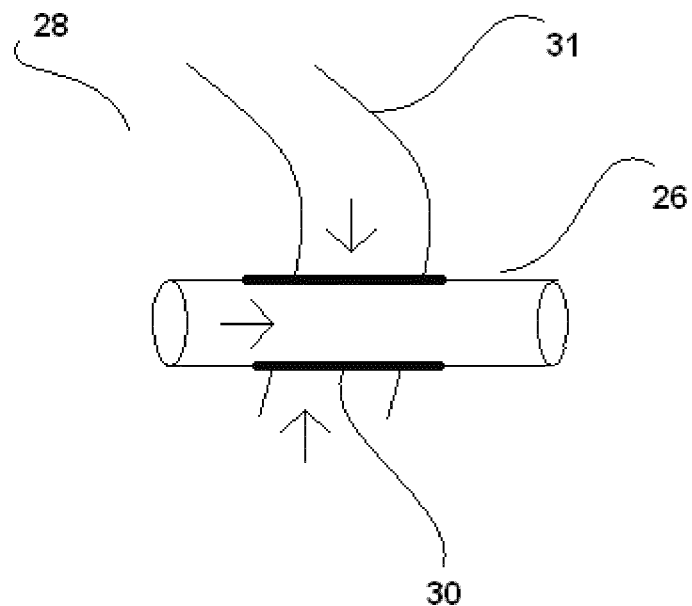

When the pressure exerted on the flexible portion 20 of the shunt 26 by the fluid flowing through the shunt (horizontal arrow) is greater than the pressure exerted on the flexible portion 30 of the shunt 26 by the sclera 31 (vertical arrows), the flexible portion 30 increases in diameter, increasing flow through the shunt 26 (FIG. 17C). The increased flow results in aqueous humor leaving the anterior chamber 28 at an increased rate.

The invention encompasses shunts of different shapes and different dimensions, and the shunts of the invention may be any shape or any dimension that may be accommodated by the eye. In certain embodiments, the intraocular shunt is of a cylindrical shape and has an outside cylindrical wall and a hollow interior. The shunt may have an inside diameter from approximately 10 μm to approximately 250 μm, an outside diameter from approximately 100 μm to approximately 450 μm, and a length from approximately 2 mm to approximately 10 mm.

In a particular embodiments, the shunt has a length of about 6 mm and an inner diameter of about 64 μm. With these dimensions, the pressure difference between the proximal end of the shunt that resides in the anterior chamber and the distal end of the shunt that resides outside the anterior chamber is about 4.3 mmHg. Such dimensions thus allow the implant to act as a controlled valve and protect the integrity of the anterior chamber.

It will be appreciated that different dimensioned implants may be used. For example, shunts that range in length from about 2 mm to about 10 mm and have a range in inner diameter from about 10 μm to about 100 μm allow for pressure control from approximately 0.5 mmHg to approximately 20 mmHg.

The material of the flexible portion and the thickness of the wall of the flexible portion will determine how reactive the flexible portion is to the pressures exerted upon it by the surrounding tissue and the fluid flowing through the shunt. Generally, with a certain material, the thicker the flexible portion, the less responsive the portion will be to pressure. In certain embodiments, the flexible portion is a gelatin or other similar material, and the thickness of the gelatin material forming the wall of the flexible portion ranges from about 10 μm thick to about 100 μm thick.

In a certain embodiment, the gelatin used for making the flexible portion is known as gelatin Type B from bovine skin. An exemplary gelatin is PB Leiner gelatin from bovine skin, Type B, 225 Bloom, USP. Another material that may be used in the making of the flexible portion is a gelatin Type A from porcine skin, also available from Sigma Chemical. Such gelatin is available from Sigma Chemical Company of St. Louis, Mo. under Code G-9382. Still other suitable gelatins include bovine bone gelatin, porcine bone gelatin and human-derived gelatins. In addition to gelatins, the flexible portion may be made of hydroxypropyl methylcellulose (HPMC), collagen, polylactic acid, polylglycolic acid, hyaluronic acid and glycosaminoglycans.

In certain embodiments, the gelatin is cross-linked. Cross-linking increases the inter- and intramolecular binding of the gelatin substrate. Any method for cross-linking the gelatin may be used. In a particular embodiment, the formed gelatin is treated with a solution of a cross-linking agent such as, but not limited to, glutaraldehyde. Other suitable compounds for cross-linking include 1-ethyl-3-[3-(dimethyamino)propyl] carbodiimide (EDC). Cross-linking by radiation, such as gamma or electron beam (e-beam) may be alternatively employed.

In one embodiment, the gelatin is contacted with a solution of approximately 25% glutaraldehyde for a selected period of time. One suitable form of glutaraldehyde is a grade 1G5882 glutaraldehyde available from Sigma Aldridge Company of Germany, although other glutaraldehyde solutions may also be used. The pH of the glutaraldehyde solution should be in the range of 7 to 7.8 and, more particularly, 7.35-7.44 and typically approximately 7.4+/−0.01. If necessary, the pH may be adjusted by adding a suitable amount of a base such as sodium hydroxide as needed.

Methods for forming the flexible portion of the shunt are shown for example in Yu et al. (U.S. patent application number 2008/0108933), the content of which is incorporated by reference herein in its entirety. In an exemplary protocol, the flexible portion may be made by dipping a core or substrate such as a wire of a suitable diameter in a solution of gelatin. The gelatin solution is typically prepared by dissolving a gelatin powder in de-ionized water or sterile water for injection and placing the dissolved gelatin in a water bath at a temperature of approximately 55° C. with thorough mixing to ensure complete dissolution of the gelatin. In one embodiment, the ratio of solid gelatin to water is approximately 10% to 50% gelatin by weight to 50% to 90% by weight of water. In an embodiment, the gelatin solution includes approximately 40% by weight, gelatin dissolved in water. The resulting gelatin solution should be devoid of air bubbles and has a viscosity that is between approximately 200-500 cp and more particularly between approximately 260 and 410 cp (centipoise).

Once the gelatin solution has been prepared, in accordance with the method described above, supporting structures such as wires having a selected diameter are dipped into the solution to form the flexible portion. Stainless steel wires coated with a biocompatible, lubricious material such as polytetrafluoroethylene (Teflon) are preferred.

Typically, the wires are gently lowered into a container of the gelatin solution and then slowly withdrawn. The rate of movement is selected to control the thickness of the coat. In addition, it is preferred that a tube be removed at a constant rate in order to provide the desired coating. To ensure that the gelatin is spread evenly over the surface of the wire, in one embodiment, the wires may be rotated in a stream of cool air which helps to set the gelatin solution and affix film onto the wire. Dipping and withdrawing the wire supports may be repeated several times to further ensure even coating of the gelatin. Once the wires have been sufficiently coated with gelatin, the resulting gelatin films on the wire may be dried at room temperature for at least 1 hour, and more preferably, approximately 10 to 24 hours. Apparatus for forming gelatin tubes are described in Yu et al. (U.S. patent application number 2008/0108933).

Once dried, the formed flexible portions may be treated with a cross-linking agent. In one embodiment, the formed flexible portion may be cross-linked by dipping the wire (with film thereon) into the 25% glutaraldehyde solution, at pH of approximately 7.0-7.8 and more preferably approximately 7.35-7.44 at room temperature for at least 4 hours and preferably between approximately 10 to 36 hours, depending on the degree of cross-linking desired. In one embodiment, the formed flexible portion is contacted with a cross-linking agent such as gluteraldehyde for at least approximately 16 hours. Cross-linking can also be accelerated when it is performed a high temperatures. It is believed that the degree of cross-linking is proportional to the bioabsorption time of the shunt once implanted. In general, the more cross-linking, the longer the survival of the shunt in the body.

The residual glutaraldehyde or other cross-linking agent is removed from the formed flexible portion by soaking the tubes in a volume of sterile water for injection. The water may optionally be replaced at regular intervals, circulated or recirculated to accelerate diffusion of the unbound glutaraldehyde from the tube. The tubes are washed for a period of a few hours to a period of a few months with the ideal time being 3-14 days. The now cross-linked gelatin tubes may then be dried (cured) at ambient temperature for a selected period of time. It has been observed that a drying period of approximately 48-96 hours and more typically 3 days (i.e., 72 hours) may be preferred for the formation of the cross-linked gelatin tubes.

Where a cross-linking agent is used, it may be desirable to include a quenching agent in the method of making the flexible portion. Quenching agents remove unbound molecules of the cross-linking agent from the formed flexible portion. In certain cases, removing the cross-linking agent may reduce the potential toxicity to a patient if too much of the cross-linking agent is released from the flexible portion. In certain embodiments, the formed flexible portion is contacted with the quenching agent after the cross-linking treatment and, may be included with the washing/rinsing solution. Examples of quenching agents include glycine or sodium borohydride.

After the requisite drying period, the formed and cross-linked flexible portion is removed from the underlying supports or wires. In one embodiment, wire tubes may be cut at two ends and the formed gelatin flexible portion slowly removed from the wire support. In another embodiment, wires with gelatin film thereon, may be pushed off using a plunger or tube to remove the formed gelatin flexible portion.

Multi-port Shunts

Other aspects of the invention generally provide multi-port shunts. Such shunts reduce probability of the shunt clogging after implantation because fluid can enter or exit the shunt even if one or more ports of the shunt become clogged with particulate. In certain embodiments, the shunt includes a hollow body defining a flow path and more than two ports, in which the body is configured such that a proximal portion receives fluid from the anterior chamber of an eye and a distal portion directs the fluid to drainage structures associated with the intra-scleral space.

Figure 18A:
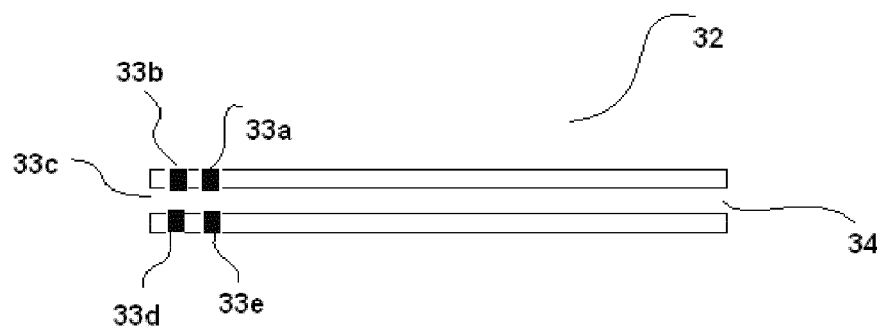
FIG. 18 shows different embodiments of multi-port shunts.
Figure 18B:
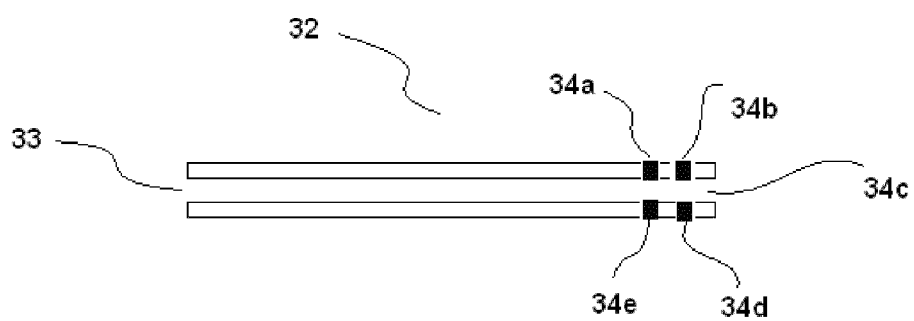
Figure 18C:
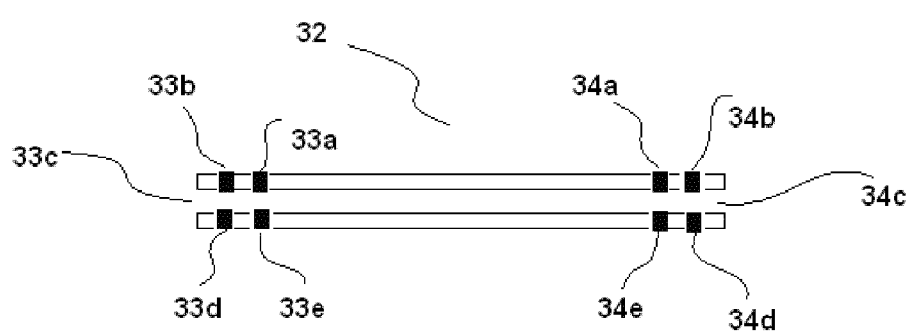

The shunt may have many different configurations. FIG. 18A shows an embodiment of a shunt 32 in which the proximal portion of the shunt (i.e., the portion disposed within the anterior chamber of the eye) includes more than one port (designated as numbers 33a to 33e) and the distal portion of the shunt (i.e., the portion that is located in the intra-scleral space) includes a single port 34. FIG. 18B shows another embodiment of a shunt 32 in which the proximal portion includes a single port 33 and the distal portion includes more than one port (designated as numbers 34a to 34e). FIG. 18C shows another embodiment of a shunt 32 in which the proximal portions include more than one port (designated as numbers 33a to 33e) and the distal portions include more than one port (designated as numbers 34a to 34e). While FIG. 18 shows shunts have five ports at the proximal portion, distal portion, or both, those shunts are only exemplary embodiments. The ports may be located along any portion of the shunt, and shunts of the invention include all shunts having more than two ports. For example, shunts of the invention may include at least three ports, at least four ports, at least five ports, at least 10 ports, at least 15 ports, or at least 20 ports.

The ports may be positioned in various different orientations and along various different portions of the shunt. In certain embodiments, at least one of the ports is oriented at an angle to the length of the body. In certain embodiments, at least one of the ports is oriented 90° to the length of the body. See for example FIG. 18A, which depicts ports 33a, 33b, 33d, and 33e as being oriented at a 90° angle to port 33c.

Figure 19A:
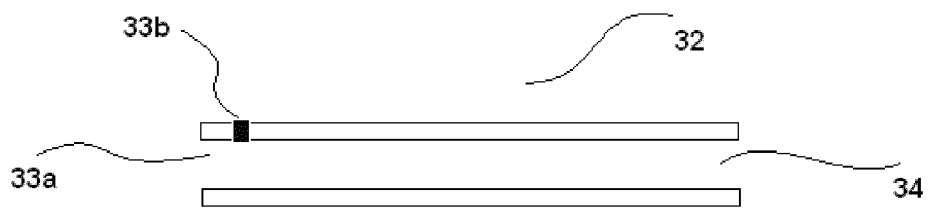
FIGS. 19A and 19B show different embodiments of multi-port shunts having different diameter ports.
Figure 19B:
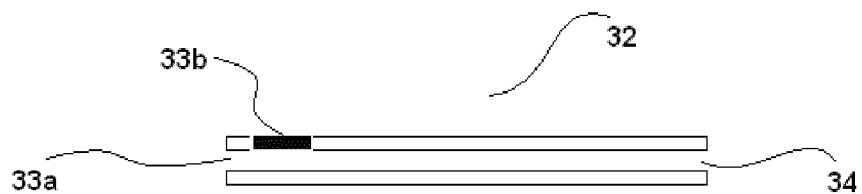

The ports may have the same or different inner diameters. In certain embodiments, at least one of the ports has an inner diameter that is different from the inner diameters of the other ports. FIG. 19A shows an embodiment of a shunt 32 having multiple ports (33a and 33b) at a proximal end and a single port 34 at a distal end. FIG. 19A shows that port 33b has an inner diameter that is different from the inner diameters of ports 33a and 34. In this figure, the inner diameter of port 33b is less than the inner diameter of ports 33a and 34. An exemplary inner diameter of port 33b is from about 20 μm to about 40 μm, particularly about 30 μm. In other embodiments, the inner diameter of port 33b is greater than the inner diameter of ports 33a and 34. See for example FIG. 19B.

The invention encompasses shunts of different shapes and different dimensions, and the shunts of the invention may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm. Shunts of the invention may be made from any biocompatible material. An exemplary material is gelatin. Methods of making shunts composed of gelatin are described above.

Shunts with Overflow Ports

Other aspects of the invention generally provide shunts with overflow ports. Those shunts are configured such that the overflow port remains partially or completely closed until there is a pressure build-up within the shunt sufficient to force open the overflow port. Such pressure build-up typically results from particulate partially or fully clogging an entry or an exit port of the shunt. Such shunts reduce probability of the shunt clogging after implantation because fluid can enter or exit the shunt by the overflow port even in one port of the shunt becomes clogged with particulate.

Figure 20A:
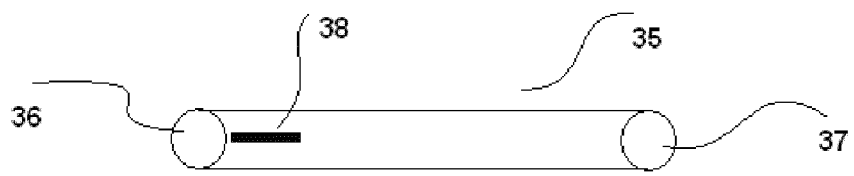
FIGS. 20A, 20B and 20C provide schematics of shunts having a slit located along a portion of the length of the shunt.
Figure 20B:
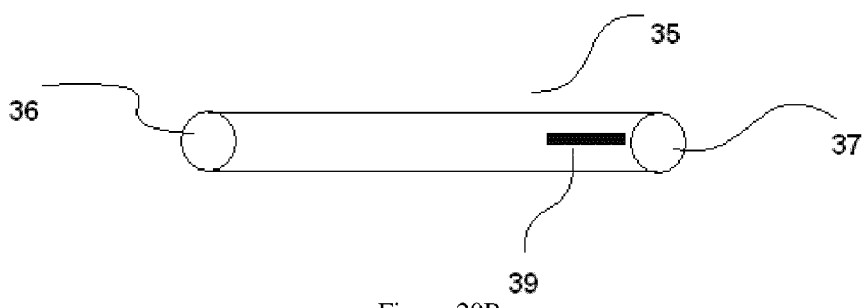
Figure 20C:
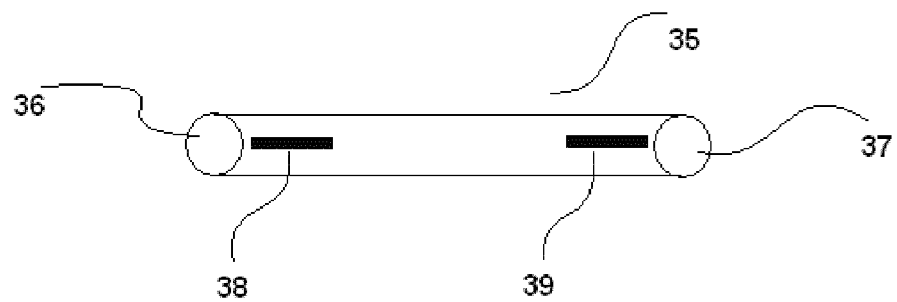

In certain embodiments, the shunt includes a hollow body defining an inlet configured to receive fluid from an anterior chamber of an eye and an outlet configured to direct the fluid to the intra-scleral space, the body further including at least one slit. The slit may be located at any place along the body of the shunt. FIG. 20A shows a shunt 35 having an inlet 36, an outlet 37, and a slit 38 located in proximity to the inlet 36. FIG. 20B shows a shunt 35 having an inlet 36, an outlet 37, and a slit 39 located in proximity to the outlet 37. FIG. 20C shows a shunt 35 having an inlet 36, an outlet 37, a slit 38 located in proximity to the inlet 36, and a slit 39 located in proximity to the outlet 37.

Figure 21:
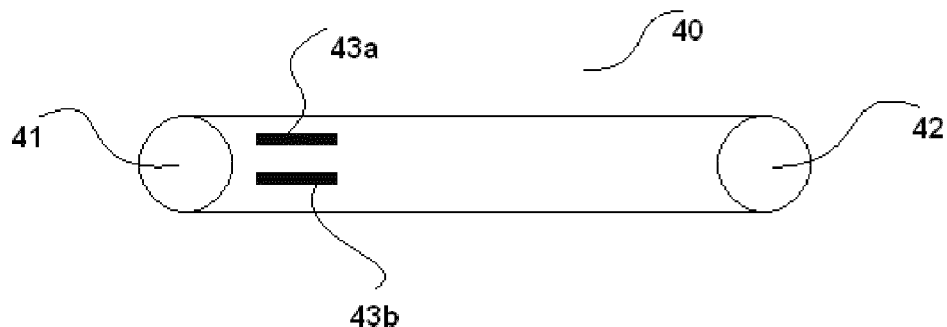
FIG. 21 depicts a shunt having multiple slits along a length of the shunt.

While FIG. 20 shows shunts have only a single overflow port at the proximal portion, the distal portion, or both the proximal and distal portions, those shunts are only exemplary embodiments. The overflow port(s) may be located along any portion of the shunt, and shunts of the invention include shunts having more than one overflow port. In certain embodiments, shunts of the invention include more than one overflow port at the proximal portion, the distal portion, or both. For example, FIG. 21 shows a shunt 40 having an inlet 41, an outlet 42, and slits 43a and 43b located in proximity to the inlet 41. Shunts of the invention may include at least two overflow ports, at least three overflow ports, at least four overflow ports, at least five overflow ports, at least 10 overflow ports, at least 15 overflow ports, or at least 20 overflow ports. In certain embodiments, shunts of the invention include two slits that overlap and are oriented at 90° to each other, thereby forming a cross.

Figure 22:
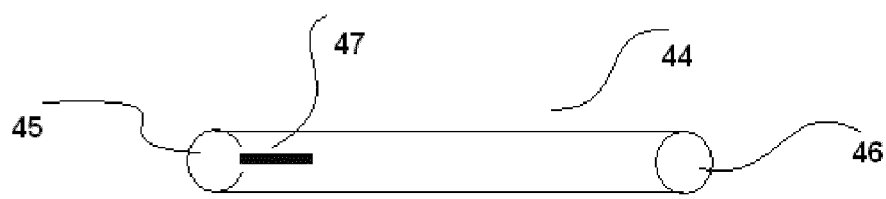
FIG. 22 depicts a shunt having a slit at a proximal end of the shunt.

In certain embodiments, the slit may be at the proximal or the distal end of the shunt, producing a split in the proximal or the distal end of the implant. FIG. 22 shows an embodiment of a shunt 44 having an inlet 45, outlet 46, and a slit 47 that is located at the proximal end of the shunt, producing a split in the inlet 45 of the shunt.

In certain embodiments, the slit has a width that is substantially the same or less than an inner diameter of the inlet. In other embodiments, the slit has a width that is substantially the same or less than an inner diameter of the outlet. In certain embodiments, the slit has a length that ranges from about 0.05 mm to about 2 mm, and a width that ranges from about 10 µm to about 200 µm. Generally, the slit does not direct the fluid unless the outlet is obstructed. However, the shunt may be configured such that the slit does direct at least some of the fluid even if the inlet or outlet is not obstructed.

The invention encompasses shunts of different shapes and different dimensions, and the shunts of the invention may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm. Shunts of the invention may be made from any biocompatible material. An exemplary material is gelatin. Methods of making shunts composed of gelatin are described above.

Shunts having a Variable Inner Diameter

In other aspects, the invention generally provides a shunt having a variable inner diameter. In particular embodiments, the diameter increases from inlet to outlet of the shunt. By having a variable inner diameter that increases from inlet to outlet, a pressure gradient is produced and particulate that may otherwise clog the inlet of the shunt is forced through the inlet due to the pressure gradient. Further, the particulate will flow out of the shunt because the diameter only increases after the inlet.

Figure 23:
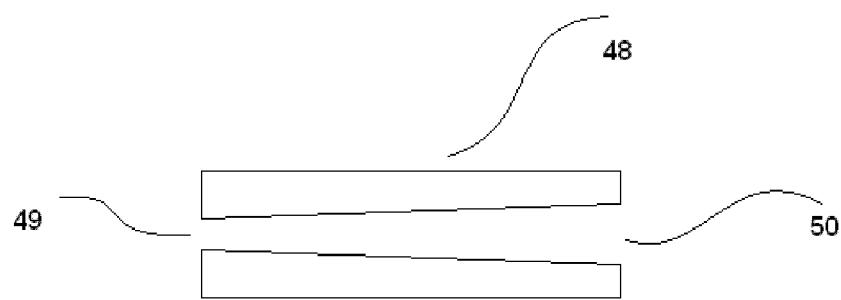
FIG. 23 provides a schematic of a shunt that has a variable inner diameter.

FIG. 23 shows an embodiment of a shunt 48 having an inlet 49 configured to receive fluid from an anterior chamber of an eye and an outlet 50 configured to direct the fluid to a location of lower pressure with respect to the anterior chamber, in which the body further includes a variable inner diameter that increases along the length of the body from the inlet 49 to the outlet 50. In certain embodiments, the inner diameter continuously increases along the length of the body, for example as shown in FIG. 23. In other embodiments, the inner diameter remains constant along portions of the length of the body.

In exemplary embodiments, the inner diameter may range in size from about 10 µm to about 200 µm, and the inner diameter at the outlet may range in size from about 15 µm to about 300 µm. The invention encompasses shunts of different shapes and different dimensions, and the shunts of the invention may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm. Shunts of the invention may be made from any biocompatible material. An exemplary material is gelatin. Methods of making shunts composed of gelatin are described above.

Shunts having Pronged Ends

In other aspects, the invention generally provides shunts for facilitating conduction of fluid flow away from an organ, the shunt including a body, in which at least one end of the shunt is shaped to have a plurality of prongs. Such shunts reduce probability of the shunt clogging after implantation because fluid can enter or exit the shunt by any space between the prongs even if one portion of the shunt becomes clogged with particulate.

FIGS. 24A-D show embodiments of a shunt 52 in which at least one end of the shunt 52 includes a plurality of prongs 53a-d. FIGS. 14A-D show an embodiment in which both a proximal end and a distal end of the shunt are shaped to have the plurality of prongs. However, numerous different configurations are envisioned. For example, in certain embodiments, only the proximal end of the shunt is shaped to have the plurality of prongs. In other embodiments, only the distal end of the shunt is shaped to have the plurality of prongs.

Figure 24A:
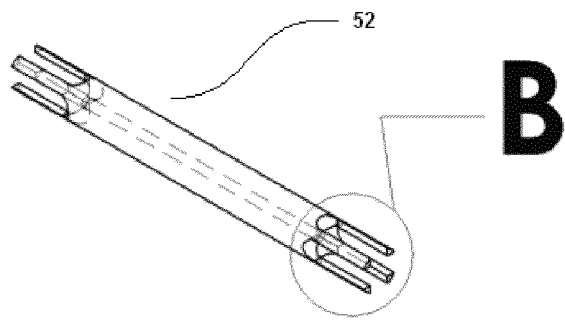
FIGS. 24A-D depict a shunt having multiple prongs at a distal and/or proximal end.
Figure 24B:
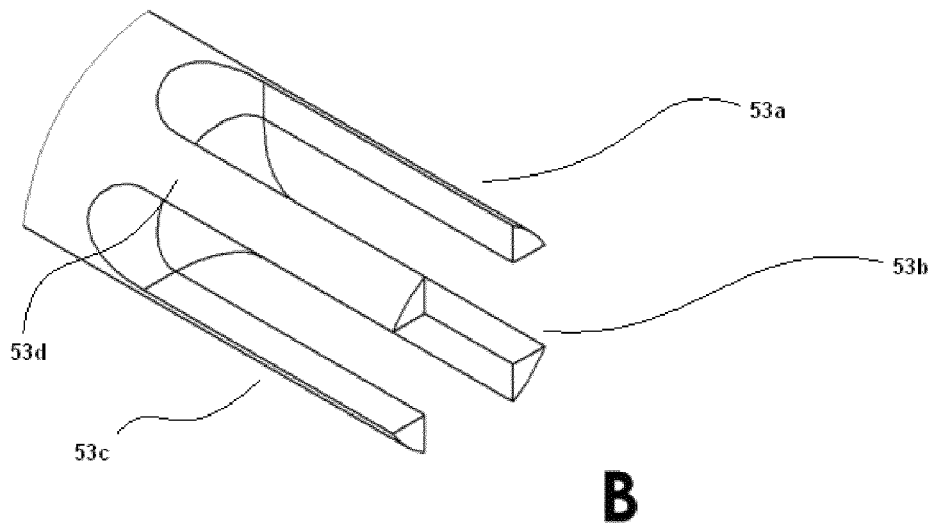
Figure 24C:
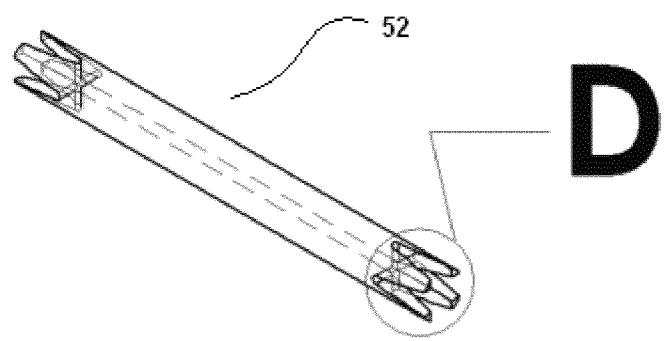
Figure 24D:
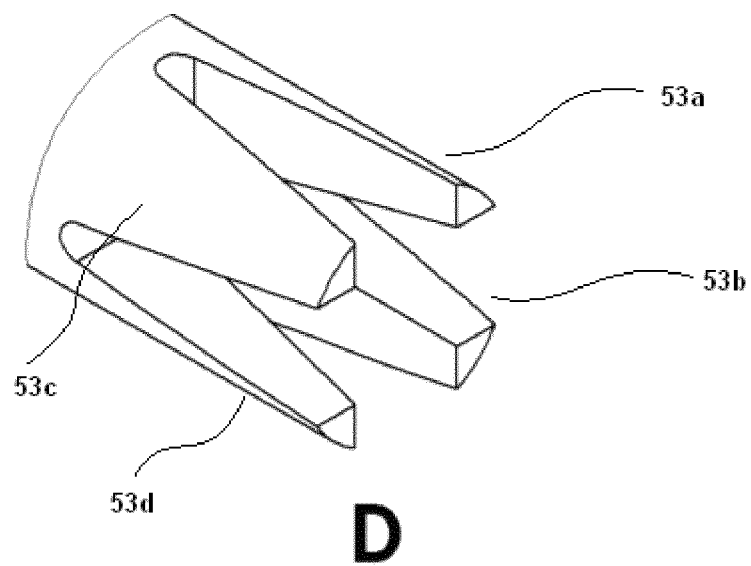

Prongs 53*a-d* can have any shape (i.e., width, length, height). FIGS. 24A-B show prongs 53*a-d* as straight prongs. In this embodiment, the spacing between the prongs 53*a-d* is the same. In another embodiment shown in FIGS. 14C-D, prongs 53*a-d* are tapered. In this embodiment, the spacing between the prongs increases toward a proximal and/or distal end of the shunt 52.

FIGS. 24A-D show embodiments that include four prongs. However, shunts of the invention may accommodate any number of prongs, such as two prongs, three prongs, four prongs, five prongs, six prongs, seven prongs, eight prongs, nine prongs, ten prongs, etc. The number of prongs chosen will depend on the desired flow characteristics of the shunt.

The invention encompasses shunts of different shapes and different dimensions, and the shunts of the invention may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm. Shunts of the invention may be made from any biocompatible material. An exemplary material is gelatin. Methods of making shunts composed of gelatin are described above.

Shunts having a Longitudinal Slit

In other aspects, the invention generally provides a shunt for draining fluid from an anterior chamber of an eye that includes a hollow body defining an inlet configured to receive fluid from an anterior chamber of the eye and an outlet configured to direct the fluid to a location of lower pressure with respect to the anterior chamber; the shunt being configured such that at least one end of the shunt includes a longitudinal slit. Such shunts reduce probability of the shunt clogging after implantation because the end(s) of the shunt can more easily pass particulate which would generally clog a shunt lacking the slits.

FIGS. 25A-D show embodiments of a shunt 54 in which at least one end of the shunt 54 includes a longitudinal slit 55 that produces a top portion 56*a* and a bottom portion 56*b* in a proximal and/or distal end of the shunt 54. FIGS. 25A-D show an embodiment in which both a proximal end and a distal end include a longitudinal slit 55 that produces a top portion 56*a* and a bottom portion 56*b* in both ends of the shunt 54. However, numerous different configurations are envisioned. For example, in certain embodiments, only the proximal end of the shunt includes longitudinal slit 55. In other embodiments, only the distal end of the shunt includes longitudinal slit 55.

Figure 25A:
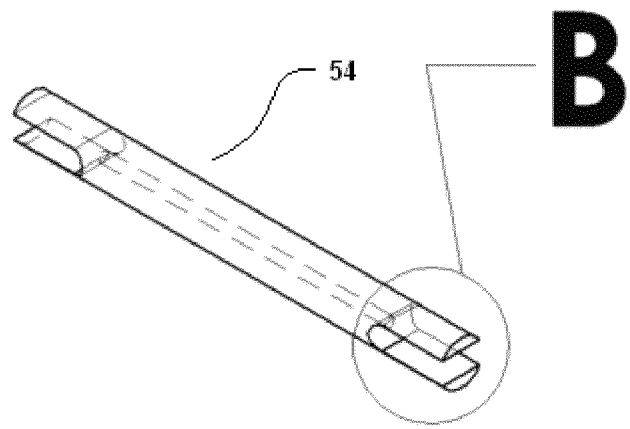
FIGS. 25A-D depict a shunt having a longitudinal slit at a distal and/or proximal end.
Figure 25B:
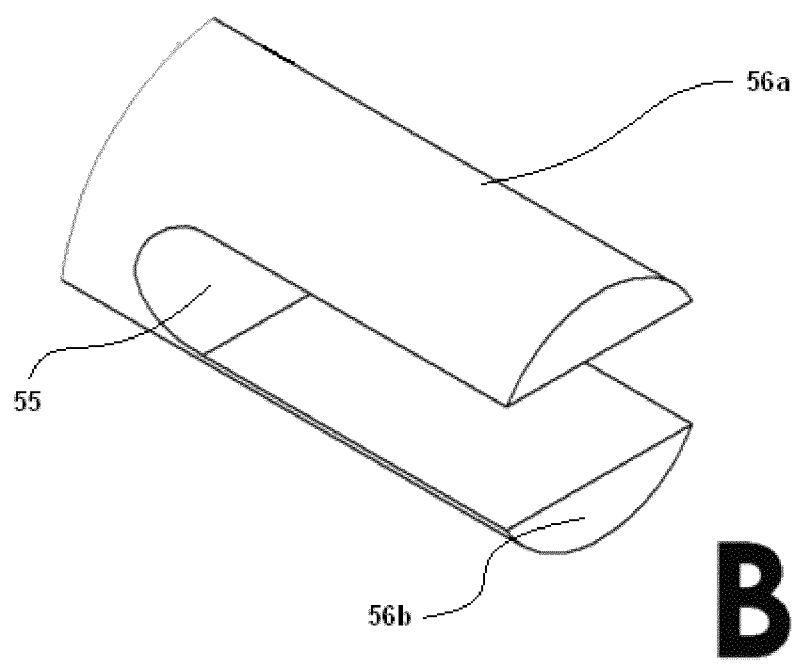
Figure 25C:
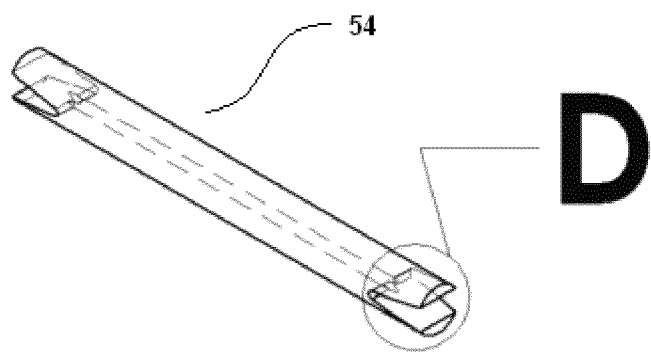
Figure 25D:
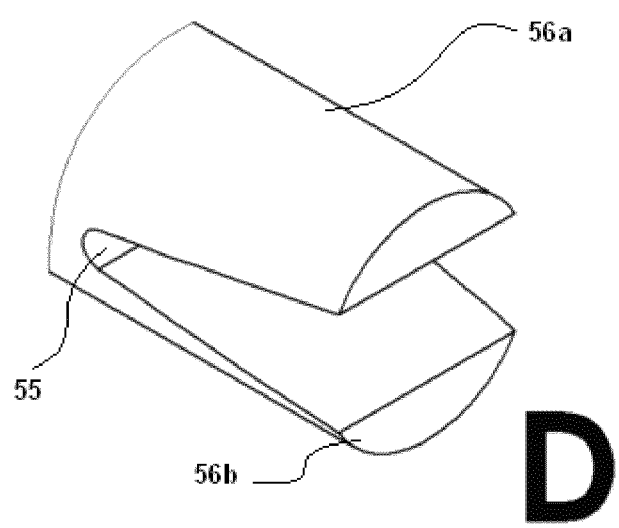

Longitudinal slit 55 can have any shape (i.e., width, length, height). FIGS. 25A-B show a longitudinal slit 55 that is straight such that the space between the top portion 56*a* and the bottom portion 56*b* remains the same along the length of the slit 55. In another embodiment shown in FIGS. 25C-D, longitudinal slit 55 is tapered. In this embodiment, the space between the top portion 45*a* and the bottom portion 56*b* increases toward a proximal and/or distal end of the shunt 54.

The invention encompasses shunts of different shapes and different dimensions, and the shunts of the invention may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm. Shunts of the invention may be made from any biocompatible material. An exemplary material is gelatin. Methods of making shunts composed of gelatin are described above.

Pharmaceutical Agents

In certain embodiments, shunts of the invention may be coated or impregnated with at least one pharmaceutical and/or biological agent or a combination thereof. The pharmaceutical and/or biological agent may coat or impregnate an entire exterior of the shunt, an entire interior of the shunt, or both. Alternatively, the pharmaceutical or biological agent may coat and/or impregnate a portion of an exterior of the shunt, a portion of an interior of the shunt, or both. Methods of coating and/or impregnating an intraocular shunt with a pharmaceutical and/or biological agent are known in the art. See for example, Darouiche (U.S. Pat. Nos. 7,790,183; 6,719,991; 6,558,686; 6,162,487; 5,902,283; 5,853,745; and 5,624,704) and Yu et al. (U.S. patent application serial number 2008/0108933). The content of each of these references is incorporated by reference herein its entirety.

In certain embodiments, the exterior portion of the shunt that resides in the anterior chamber after implantation (e.g., about 1 mm of the proximal end of the shunt) is coated and/or impregnated with the pharmaceutical or biological agent. In other embodiments, the exterior of the shunt that resides in the scleral tissue after implantation of the shunt is coated and/or impregnated with the pharmaceutical or biological agent. In other embodiments, the exterior portion of the shunt that resides in the intra-scleral space after implantation is coated and/or impregnated with the pharmaceutical or biological agent. In embodiments in which the pharmaceutical or biological agent coats and/or impregnates the interior of the shunt, the agent may be flushed through the shunt and into the area of lower pressure (e.g., the intra-scleral space).

Any pharmaceutical and/or biological agent or combination thereof may be used with shunts of the invention. The pharmaceutical and/or biological agent may be released over a short period of time (e.g., seconds) or may be released over longer periods of time (e.g., days, weeks, months, or even years). Exemplary agents include anti-mitotic pharmaceuticals such as Mitomycin-C or 5-Fluorouracil, anti-VEGF (such as Lucintes, Macugen, Avastin, VEGF or steroids).

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A device for deploying an intraocular shunt, the device comprising:
   a hollow sleeve;
   a flexible hollow shaft in the sleeve, the shaft having a curved configuration while outside the sleeve and a less curved configuration, less curved than the curved configuration, while inside the sleeve; and
   an intraocular shunt within the shaft;
   wherein the shaft, when in the curved configuration, is configured to guide the shunt along a scleral spur of an eye as the shunt is exposed from the shaft;
   wherein the shaft is configured to be withdrawn, in the less curved configuration, from the eye after the shunt is exposed from the shaft such that a distal portion of the shunt resides in the suprachoroidal space and a proximal portion of shunt resides in the anterior chamber.

2. The device according to claim 1, wherein the housing comprises a proximal portion and a distal portion and the distal portion is movable within the proximal portion.

3. The device according to claim 2, wherein the distal portion of the housing comprises a stiff sleeve and the shaft is movably disposed within the sleeve.

4. The device according to claim 2, wherein the shaft comprises a curved portion, the curved portion being configured to match an angle of the sclera.

5. The device according to claim 2, wherein a distal end of the hollow shaft comprises a sharp tip.

6. The device according to claim 2, wherein a distal end of the sleeve comprises a protrusion.

7. The device according to claim 6, wherein the protrusion provides resistance against advancement of the device when the protrusion contacts scleral tissue on an inside of an anterior chamber.

8. The device according to claim 6, wherein the protrusion comprises a flat bottom portion and an angled top portion.

9. The device according to claim 8, wherein the angle of the top portion is substantially identical to an anterior chamber angle of an eye.

10. The device according to claim 1, wherein the shunt is a soft gel shunt.

11. A method for implanting a shunt in a suprachoroidal space of an eye, the method comprising:
    providing a device comprising: a housing; a deployment mechanism at least partially disposed within the housing; and a flexible hollow shaft coupled to the deployment mechanism and disposed within the shaft in a less curved configuration, less curved than the curved configuration, wherein the shaft holds an intraocular shunt, and is configured to guide the shunt along a scleral spur of an eye as the shunt is exposed from the shaft;
    inserting the device into the eye;
    advancing the shaft out of the housing, whereby the shaft transitions from the less curved configuration to a curved configuration; and
    exposing the shunt from the shaft along a curved pathway, defined by the shaft in the curved configuration, within the eye such that a proximal portion of the shunt resides in and receives fluid from an anterior chamber of an eye and a distal portion of the shunt resides in and directs the fluid to the suprachoroidal space.

12. The method of claim 11, wherein the inserting step comprises insertion of the device into eye tissue.

13. The method of claim 12, wherein the insertion comprises inserting the device into the eye anterior to the corneal limbus.

14. The method of claim 12, wherein the insertion comprises inserting the device into the eye posterior to the corneal limbus.

15. The method of claim 11, wherein the inserting occurs without removing a portion of the trabecular meshwork or the iris.

16. The method of claim 11, wherein the method is performed without inducing subconjunctival blebbing.

17. The method according to claim 11, wherein prior to the exposing step, the method further comprises injecting a drug into the suprachoroidal space.

18. The method according to claim 17, wherein the drug is a steroid or antifibrotic agent.

19. The method according to claim 11, further comprising withdrawing the shaft into the sleeve, whereby the shaft changes from the curved configuration to the less curved configuration.

* * * * *